US008465738B2

(12) United States Patent
Lyden et al.

(10) Patent No.: US 8,465,738 B2
(45) Date of Patent: Jun. 18, 2013

(54) USE OF VASCULAR ENDOTHELIAL GROWTH FACTOR RECEPTOR 1+ CELLS IN TREATING AND MONITORING CANCER AND IN SCREENING FOR CHEMOTHERAPEUTICS

(75) Inventors: David Lyden, New York, NY (US); Rosandra N. Kaplan, New York, NY (US); Rebecca D. Riba, New York, NY (US); Shahin Rafii, Great Neck, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 241 days.

(21) Appl. No.: 12/564,683

(22) Filed: Sep. 22, 2009

(65) Prior Publication Data
US 2010/0150932 A1  Jun. 17, 2010

Related U.S. Application Data

(62) Division of application No. 11/284,265, filed on Nov. 21, 2005, now Pat. No. 7,598,043.

(60) Provisional application No. 60/629,662, filed on Nov. 19, 2004, provisional application No. 60/723,770, filed on Oct. 5, 2005.

(51) Int. Cl.
*A61K 39/395* (2006.01)

(52) U.S. Cl.
USPC ........................................ 424/130.1; 435/7.1

(58) Field of Classification Search
None
See application file for complete search history.

(56) References Cited

U.S. PATENT DOCUMENTS

| 6,448,077 | B1 * | 9/2002 | Rockwell et al. | 435/334 |
| 6,617,160 | B1 | 9/2003 | Shitara et al. | |
| 6,811,779 | B2 | 11/2004 | Rockwell et al. | |
| 7,824,680 | B2 * | 11/2010 | Varner | 424/143.1 |
| 2003/0180286 | A1 * | 9/2003 | Carmeliet et al. | 424/130.1 |

FOREIGN PATENT DOCUMENTS

| WO | 98/22616 A1 | 5/1998 |
| WO | 02/070008 A1 | 9/2002 |
| WO | WO 03/006059 | 1/2003 |
| WO | WO 03/014326 | 2/2003 |
| WO | WO 03/019136 | 3/2003 |
| WO | 03/075841 A2 | 9/2003 |

OTHER PUBLICATIONS

Hessig et al, Cell, 2002, 109:625-637.*
European Examination Report Dated Feb. 11, 2010.
Kaplan et al., "Leptomeningeal Metastases: Comparison of Clinical Features and Laboratory data of Solid Tumors, Lymphomas and Leukemias," J. Neuro-Oncol. 9:225-229 (1990).
"Adult Acute Myeloid Leukemia Treatment (PDQ)," National Cancer Institute (Patient Version) http://www.cancer.gov/cancertopics/pdq/treatment/adultAML/Patient/page2.
Eriksson et. al., "Placenta Growth Factor-1 Antagonizes VEGF-Induced Angiogenesis and Tumor Growth by the Formation of Functionally Inactive PIGF-1/VEGF Heterodimers," Cancer Cell 1:99-108 (2002).
First Office Action for Chinese Patent Application No. 200580046852.3 (Aug. 7, 2009).
International Search Report for PCT/US05/42125 (Nov. 2, 2006).
Kaplan et al., "Recruitment of VEGFR1+ Hematopoietic Progenitors Contributes to the Establishment of Tumor Metastasis," Abstract of Presentation at Keystone Symposia Angiogenesis: Novel Basic Science Insights and Human Therapy (A5), Santa Fe, New Mexico (Jan. 15, 2004).
Kaplan et al., "VEGFR1-Positive Haematopoietic Bone Marrow Progenitors Initiate the Pre-Metastatic Niche," with Supplementary Materials, Nature 438(8):820-827 (2005).
Lyden, David C., "Recruitment of VEGFR1+ Hematopoietic Progenitors Contributes to the Establishment of Tumor Metastasis," Short Talk Presented at Keystone Symposia Meeting, Angiogenesis: Novel Basic Science Insights and Human Therapy (A5), Santa Fe, New Mexico (Jan. 15, 2004).
Second Office Action for Chinese Patent Application No. 200580046852.3 (Jul. 30, 2010).
Viglietto et. al., "Upregulation of Vascular Endothelial Growth Factor (VEGF) and Downregulation of Placenta Growth Factor (PIGF) Associated With Malignancy in Human Thyroid Tumors and Cell Lines," Oncogene 11:1569-79 (1995).
Written Opinion for PCT/US05/42125 (Nov. 2, 2006).
Hiratsuka et al., "MMP9 Induction by Vascular Endothelial Growth Factor Receptor-1 Is Involved in Lung-Specific Metastasis," Cancer Cell 2:289-300 (2002).
Hattori et al., Nature Medicine 8:841-849 (2002).
Chen et al., Cancer Lett. 213:73-82 (2004).
Lyden et al., "Impaired Recruitment of Bone-Marrow-Derived Endothelial and Hematopoietic Precursor Cells Blocks Tumor Angiogenesis and Growth," Nat. Med. 7(11):1194-1201 (2001).
Wu et al., "Monoclonal Antibody Against VEGFR1 Inhibits FLT1-Positive Breast Tumor Growth by a Dual Mechanism Involving Anti-Endothelial and Anti-Tumor Cell Growth Activities," Proceedings of the Annual Meeting of The American Association for Cancer Research, New York, NY 43:527 (2002).

(Continued)

Primary Examiner — Mark Halvorson
(74) Attorney, Agent, or Firm — LeClairRyan, a Professional Corporation

(57) ABSTRACT

The present invention is directed to a method of inhibiting tumor formation in a cancer patient at a site remote from sites of prior tumor formation and to a method of preventing metastases. These methods involve administering to the cancer patient an inhibitor of vascular endothelial growth factor receptor 1$^+$ bone marrow-derived cells under conditions effective either to inhibit tumor formation in the cancer patient at a site remote from sites of prior tumor formation or to prevent metastases. Candidate compounds useful for such purposes can be screened depending on whether they bind to vascular endothelial growth factor receptor 1$^+$ bone marrow-derived cells. Metastases in a cancer patient can be monitored by evaluating a patient sample for detection and quantification of vascular endothelial growth factor receptor 1$^+$ bone marrow-derived cells and comparing the level of vascular endothelial growth factor receptor 1$^+$ bone marrow-derived cells to prior levels.

40 Claims, 20 Drawing Sheets

OTHER PUBLICATIONS

Dias et al., "Neutralizing MOAB to VERGF Receptors Inhibit Proliferation and Migration of a Sudset of Human Leukemias Through Interaction with VERGFR-2 (KDR) and VEGFR-1 (FLT-1)," Blood 94(10):620A (1999).

Kaplan, et al., "VEGFR1-Positive Haematopoietic Bone Marrow Progenitors Initiate the Pre-Metastatic Niche," Nature 438(7069):820-827 (2005).

Yang et al., "Vascular Endothelial Growth Factor Receptor-1 Activation Mediates Epithelial to Mesenchymal Transition in Human Pancreatic Carcinoma Cells," Cancer Research 66(1):46-51 (2006).

Depalma et al., Targeting Exogenous Genes to Tumor Angiogenesis by Transplantation of Genetically Modified Hematopoietic Stem Cells, Nature Medicine 9(6):789-795 (2003).

European Search Report for corresponding EP Application No. 05856987.2 (Dated: Jun. 8, 2009).

Chinese Office Action for Chinese Patent Application No. 200580046852 dated Jan. 26, 2011.

Japanese Notice of Reasons for Rejection for Japanese Patent Application No. 2007-543341 dated Jun. 30, 2011.

Davidoff et al., "Bone Marrow-Derived Cells Contribute to Tumor Neovasculature and, When Modified to Express an Angiogensis Inhibitor, can Restrict Tumor Growth in Mice," Clin. Cancer Res. 7:2870-2879 (2001).

Examination Report for corresponding Japanese patent application No. 2007-543341 (Feb. 2, 2012).

Decision of Rejection for corresponding Japanese patent application No. 2007-543341 (Jun. 4, 2012).

Otorhinolaryngology 40(4):386-394 (1997).

Examination Report for corresponding Chinese patent application No. 200580046852.3 (Oct. 26, 2011).

Ruggeri et al., "CEP-7055: A Novel, Orally, Active Pan Inhibitor of Vascular Endothelial Growth Factor Receptor Tyrosine Kinases with Potent Antiangiogenic Activity and Antitumor Efficacy in Preclinical Models," Cancer Res. 63 (18):5978-91 (2003).

Thomas et al., "Vascular Endothelial Growth Factor Receptor Tyrosine Kinase Inhibitors: PTK787/ZK 222584" Semin. Oncol. 30(3 Suppl 6):32-8 (2003) (Abstract).

Drevs et al., "PTK787/Zk 222584, a Specific Vascular Endothelial Growth Factor-Receptor Tyrosine Kinase Inhibitor, Affects the Anatomy of the Tumor Vascular Bed and the Functional Vascular Properties as Detected by Dynamic Enhanced Magnetic Resonance Imaging," Cancer Res. 62:4015-4022 (2002).

Wood et al., "PTK787/Zk 222584, a Novel and Potent Inhibitor of Vascular Endothelial Growth Factor Receptor Tyrosine Kinases, Impairs Vascular Endothelial Growth Factor-Induced Responses and Tumor Growth After Oral Administration," Cancer Res. 60:2178-2189 (2000).

Patel et al., "A Selective and Oral Small Molecule Inhibitor of Vascular Epithelial Growth Factor Receptor (VEGFR)-2 and VEGFR-1 Inhibits Neovascularization and Vascular Permeability," J. Pharm. Exp. Therap. 306(3):838-45 (2003).

An et al., "Suppression of Tumor Growth and Metastasis by a VEGFR-1 Antagonizing Peptide Identified from a Phage Display Library," Int. J. Cancer 111(2):165-73 (2004).

Luttun et al., "Revascularization of Ischemic Tissues by PIGF Treatment, and Inhibition of Tumor Angiogenesis, Arthritis and Atherosclerosis by Anti-Flt1," Nat. Med. 8(8):831-40 (2002) (Abstract).

Van der Laan et al., "Beneficial Effect of Modified Peptide Inhibitor of Alpha4 Integrins on Experimental Allergic Encephalomyelitis in Lewis Rats," J. Neurosci. Res. 67(2):191-9 (2002) (Abstract).

Hagmann et al., "The Discovery of Sulfonylated Dipeptides as Potent VLA-4 Antagonists," Bioorg. Med. Chem. Lett. 11 (20):2709-13 (2001) (Abstract).

Abraham et al., "A Small-Molecule, Tight-Binding Inhibitor of the Integrin Alpha(4)Beta(1) Blocks Antigen-Induced Airway Responses and Inflammation in Experimental Asthma in Sheep," Am. J. Respir. Crit Care Med. 162(2 Pt 1):603-11 (2000).

Haworth et al., "Anti-Inflammatory Activity of c(ILDV-NH(CH2)5CO), a Novel, Selective, Cyclic Peptide Inhibitor of VLA-4-Mediated Cell Adhesion," Br. J. Pharmacol. 126(8):1751-60 (1999).

Piraino et al., "Prolonged Reversal of Chronic Experimental Allergic Encephalomyelitis Using a Small Molecule Inhibitor of Alpha4 Integrin," J. Neuroimmunol. 131(1-2):147-59 (2002) (Abstract).

Leone et al., "An Assessment of the Mechanistic Differences Between Two Integrin Alpha4Beta1 Inhibitors, the Monoclonal Antibody TA-2 and the Small Molecule BIO5192, in Rat Experimental Autoimmune Encephalomyelitis," J. Pharmacol. Exp. Therap. 305(3):1150-1162 (2003).

Giraudo et al., "An Amino-Bisphosphonate Targets MMP-9-Expressing Macrophages and Angiogenesis to Impair Cervical Carcinogenesis." J. Clin. Invest. 114(5): 623-33 (2004).

Nyormoi et al., "An MMP-2/MMP-9 Inhibitor, 5a, Enhances Apoptosis Induced by Ligands of the TNF Receptor Superfamily in Cancer Cells," Cell Death Differ. 10(5):558-69 (2003).

Siu et al., "Interactions of Proteases, Protease Inhibitors, and the Beta1 Integrin/Laminin Gamma3 Protein Complex in the Regulation of Ectoplasmic Specialization Dynamics in the Rat Testis," Biol. Reprod. 70(4):945-64 (2004).

Suzuki et al., "Role of Matrix Metalloproteinase-9 in in Vitro Invasion of Esophageal Carcinoma Cells," J. Surg. Oncol. 81(2):80-86 (2002) (Abstract).

Watanabe et al., "Liver-Derived Matrix Metalloproteinase-9 (Gelatinase B) Recruits Progenitor Cells from Bone Marrow Into the Blood Circulation," Biol. Pharm. Bull. 26(4):564-8 (2003).

Ende et al., "Inhibition of Matrix Metalloproteinase-2 and -9 Activities by Selected Flavonoids," Planta Med. 70 (10):1006-8 (2004) (Abstract).

"Adult Acute Myeloid Leukemia Treatment (PDQ)," National Cancer Institute (Patient Version) http://www.cancer.gov/cancertopics/pdq/treatment/adultAML/Patient/page2, Sep. 10, 2009.

* cited by examiner

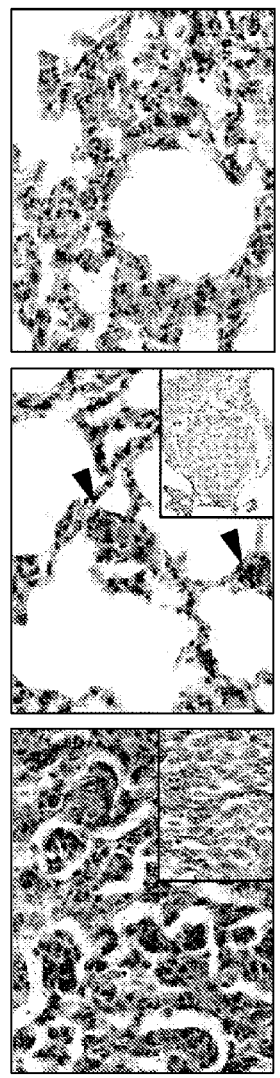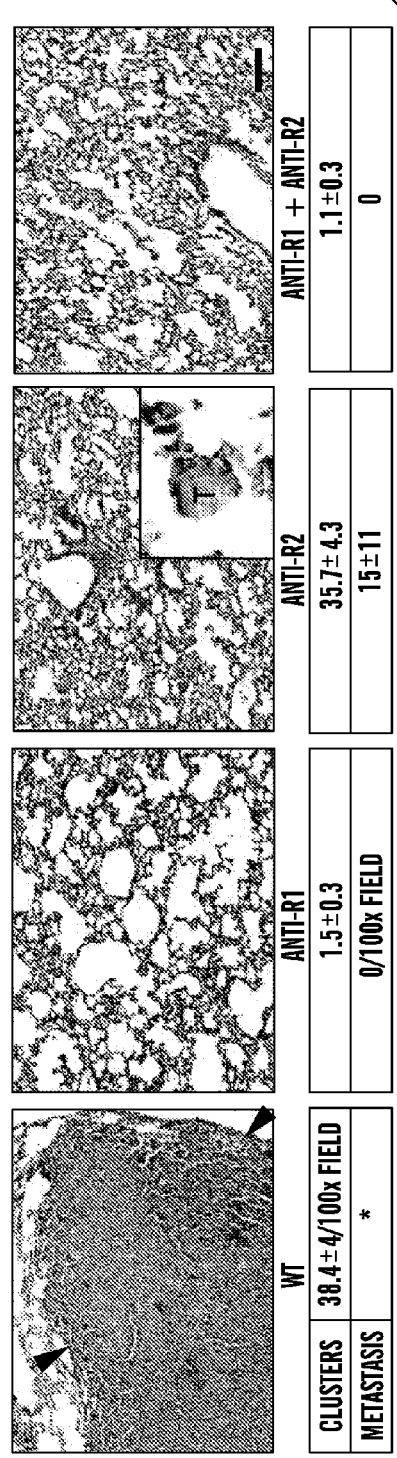
FIG. 2A
FIG. 2B

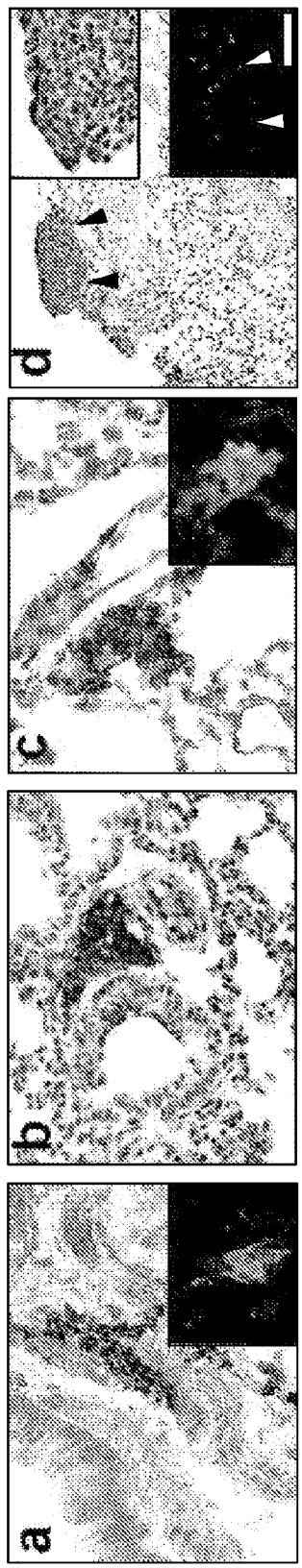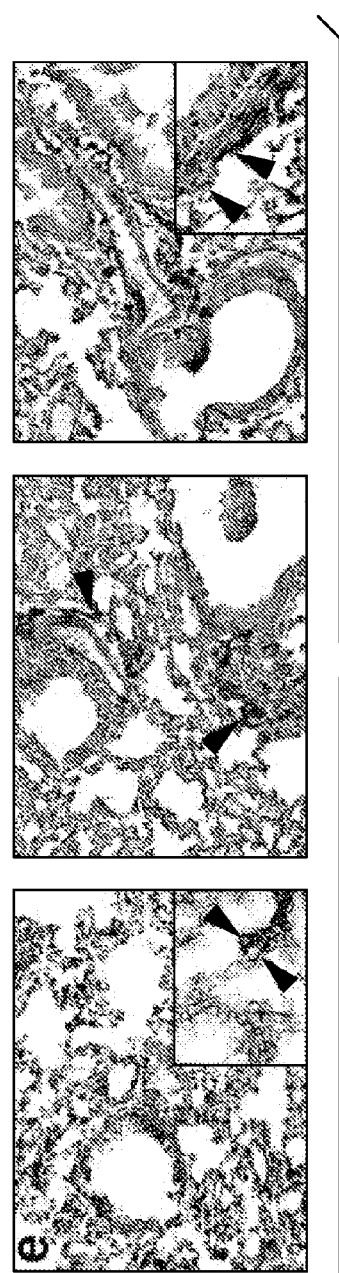
FIG. 3A  FIG. 3B  FIG. 3C  FIG. 3D
FIG. 3E

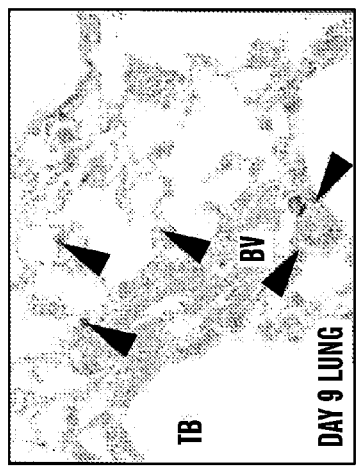
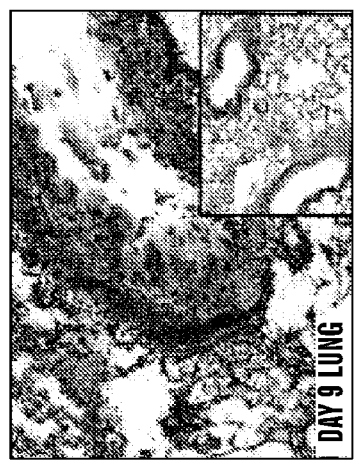
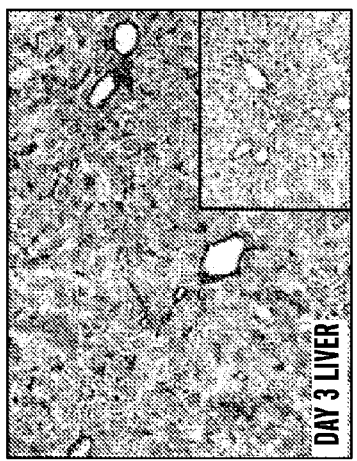
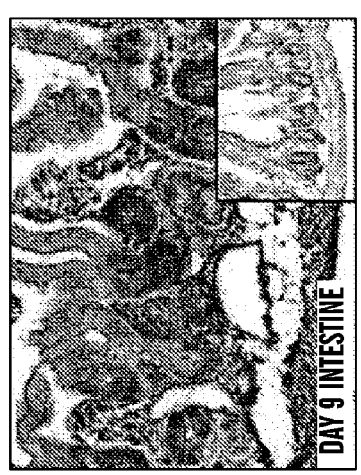
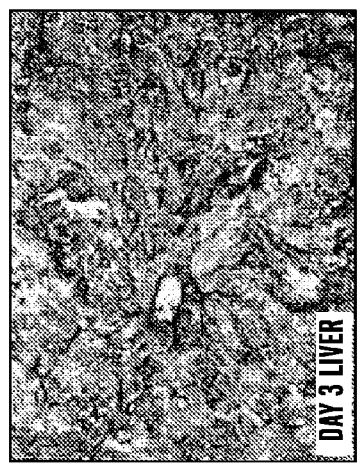
FIG. 7A
FIG. 7B

LEWIS LUNG CARCINOMA

B-16 MELANOMA

| | ANTI-VLA-4 | IgG | MMP-9 KO | CONTROL | ANTI-Id3 | Id3 -/- | Id3 -/- + VEGFR1 | CONTROL |
|---|---|---|---|---|---|---|---|---|
| CLUSTERS | 2.6±0.4 | 25.4±3.0 | 12.3±1.8 | 35.2±1.9 | 1.1±0.3 | | 63.7±4.5 | 48±3.6 |
| METASTASIS | 0.4±0.2 | 5.5±0.6 | 0.6±0.3 | 10±1.1 | 0 | | 6.5±1.1 | 6.1±1.5 |

USE OF VASCULAR ENDOTHELIAL GROWTH FACTOR RECEPTOR 1+ CELLS IN TREATING AND MONITORING CANCER AND IN SCREENING FOR CHEMOTHERAPEUTICS

This application is a division of U.S. patent application Ser. No. 11/284,265, filed Nov. 21, 2005, which claims the benefit of U.S. Provisional Patent Application Ser. Nos. 60/629,662, filed Nov. 19, 2004, and 60/723,770, filed Oct. 5, 2005, which are hereby incorporated in their entirety.

This invention was made with government support under grant number 1 R01 CA098234-01 awarded by National Institutes of Health. The government has certain rights in this invention.

FIELD OF THE INVENTION

The present invention is directed to the use of vascular endothelial growth factor receptor $1^+$ cells in treating and monitoring cancer and in screening for chemotherapeutics.

BACKGROUND OF THE INVENTION

Cancer is the second leading cause of death next to heart attacks in the United States. There has been important progress in the development of new therapies in the treatment of this devastating disease. Much of the progress is due to better understanding of cell proliferation in both normal cells and cancerous cells.

Normal cells proliferate as a result of the highly controlled activation of growth factor receptors by their respective ligands. Examples of such receptors are the growth factor receptor tyrosine kinases.

Cancer cells also proliferate as a result of DNA mutations or loss of tumor suppressor gene function in normal cells. These genetic alterations cause many new protein products, such as overexpression of tumor-associated growth factors or chemokines or receptors, that can stimulate other cells (e.g., endothelial cells) to proliferate and form the new blood vessels within the tumor for continued growth and promotion of metastasis.

Some examples of growth factor receptors found on non-tumor cells that support tumor growth and, in certain circumstances, on the surface of tumor cells themselves involve vascular endothelial growth factor receptors (VEGFRs), platelet-derived growth factor receptors (PDGFR), insulin-like growth factor receptors (IGFR), nerve growth factor receptors (NGFR), and fibroblast growth factor receptors (FGF).

During embryonic development, hematopoietic and early endothelial cells (angioblasts) originate from a common precursor cell known as hemagioblast. Because of their common cellular origin, several signaling pathways are shared by both hematopoietic and vascular cells. One such pathway is the VEGFR signaling pathway. VEGF receptors (VEGFR) include VEGFR1 (otherwise known as FLT-1), which was sequenced by Shibuya M. et al., *Oncogene* 5:519-524 (1990) and VEGFR2 (otherwise known as KDR or FLK-1), described in Terman et al., *Oncogene* 6:1677-1683 (1991); and sequenced by Matthews W. et al., *Proc. Natl. Acad. Sci. USA* 88:9026-9030 (1991).

Unless otherwise stated or clearly inferred otherwise by context, this specification will follow the customary literature nomenclature of VEGF receptors. KDR will be referred to as the human form of VEGFR2. FLK-1 will be referred to as the murine homolog of VEGFR2. FLT-1 is different from, but related to, the KDR/FLK-1 receptor.

VEGFR binds to both VEGFR1 and VEGFR2, exherting proliferative and migratory effects on endothelial and hematopoietic cells. VEGFR2 was thought to be exclusively expressed by endothelial cells. Recently, however, VEGFR2 has been shown to be present on a subset of multi-potent hematopoietic stem cells (Ziegler et al., *Science* 285(5433): 1553-8 (1999)). Several studies have revealed that certain leukemic cells also expressed VEGFR1 and VEGFR2 (Fiedler et al., *Blood* 89(6):1870-5 (1997)).

The two primary signaling tyrosine kinase receptors that mediate the various biological effects of VEGF are VEGFR2 and VEGFR1. Although the binding affinity of VEGFR1 to VEGF is very high, with Kd values of 10-70 pM (Klagsbrun et al., *Cytokine Growth Factor Rev* 7(3):259-70 (1996)), most studies have shown that VEGFR2 is the critical receptor for transmitting cellular signals for the proliferation and differentiation of endothelial cells (Ortega et al., *Am J Pathol* 151 (5):1215-24 (1997)). VEGFR1 appears to be more important for vascular remodeling. The relative significance of VEGF receptors in the regulation of vasculogenesis and angiogenesis has been established in studies in which the VEGFR2 and VEGFR1 genes were disrupted in murine embryonic stem cells by homologous recombination. Mice deficient in VEGFR2 had drastic defects in vasculogenesis, angiogenesis, and hematopoiesis (Shalaby et al., *Nature* 376(6535): 62-6 (1995)). In contrast, VEGFR1 knockout mice developed abnormal vascular channels, suggesting a role for this receptor in the regulation of cellular interactions and vascular stabilization (Fong et al., *Nature* 376(6535):66-70 (1995)).

Inhibition of angiogenesis through disruption of VEGFR2 signaling results in inhibition of growth and metastasis of solid tumors. For example, neutralizing monoclonal antibody (MoAb) to murine VEGFR2 inhibited tumor invasion in murine models (Skobe et al., *Nat Med* 3(11):1222-7 (1997) and Prewett et al., *Cancer Res* 59(20):5209-18 (1999)). Furthermore, glioblastoma growth was inhibited in mice dominant-negative for VEGFR2 (Millauer et al., *Nature* 367(6463):576-9 (1994)). Such inhibition of tumor growth is attributed to the inhibition of angiogenesis, effectively limiting the blood supply of the tumor.

Leukemias originate from hematopoietic stem cells at different stages of their maturation and differentiation. It is now well established that acute leukemias originate from immature hematopoietic stem cells that have the capacity to undergo self-renewal, whereas certain less aggressive leukemias such as chronic leukemias seem to originate from the more mature committed hematopoietic progenitor cells.

Several studies have shown that VEGF is almost invariably expressed by all established leukemic cell lines as well as freshly isolated human leukemias, including the well studied HL-60 leukemic cell line (Fiedler et al., *Blood* 89(6):1870-5 (1997), Bellamy et al., *Cancer Res* 59(3):728-33 (1999)). Using RT-PCR, several studies have shown that VEGFR-2, and VEGFR-1 are only expressed by certain human leukemias (Fiedler et al., *Blood* 89(6):1870-5 (1997), Bellamy et al., *Cancer Res* 59(3):728-33 (1999)). However, none of these studies have shown whether expression of VEGF is associated with any parallel surface VEGFR2/VEGFR1 expression or functional response.

Bone marrow (BM)-derived cells (BMDCs) can contribute to malignant conversion (Coussens et al., "MMP-9 Supplied by Bone Marrow-derived Cells Contributes to Skin Carcinogenesis," *Cell* 103:481-490 (2000)), tumor vascularization (Lyden et al., "Impaired Recruitment of Bone-marrow-derived Endothelial and Hematopoietic Precursor Cells Blocks Tumor Angiogenesis and Growth," *Nat. Med.* 7:1194-1201 (2001) and Autiero et al., "Placental Growth Factor and its Receptor, Vascular Endothelial Growth Factor Receptor-1: Novel Targets for Stimulation of Ischemic Tissue Revascularization and Inhibition of Angiogenic and Inflammatory Disorders," *Journal of Thromb. Haemost.* 1:1356-1370 (2003)), and neoplastic cell migration (Neson et al., "Lymphocyte-facilitated Tumor Cell Adhesion to Endothelial Cells: the Role of High Affinity Leukocyte Integrins," *Pathology* 35:50-55 (2003)). A population of hematopoietic progenitor cells (HPCs) expressing vascular endothelial growth factor receptor 1 (VEGFR1) whose stem cells reside in specific niche-dependent regions in the BM have previously been identified. In neoangiogenesis, this normally small population of less than 0.01% total BM cells proliferate and mobilize to the peripheral circulation along with BM-derived VEGFR2+ endothelial progenitors (EPCs), both essential for the vascularization and growth of primary tumors (Lyden et al., "Impaired Recruitment of Bone-marrow-derived Endothelial and Hematopoietic Precursor Cells Blocks Tumor Angiogenesis and Growth," *Nat. Med.* 7:1194-1201 (2001) and Hattori et al., "Placental Growth Factor Reconstitutes Hematopoiesis by Recruiting VEGFR1(+) Stem Cells from Bone-marrow Microenvironment," *Nat. Med.* 8:841-9 (2002)). These VEGFR1+ cells, which are of myelomonocytic origin, localize to perivascular sites in the tumor bed and play a supportive and stabilizing role for newly formed vessels (Lyden et al., "Impaired Recruitment of Bone-marrow-derived Endothelial and Hematopoietic Precursor Cells Blocks Tumor Angiogenesis and Growth," *Nat. Med.* 7:1194-1201 (2001)). These and other tumor-associated cells have been found to enhance primary tumor growth and promote tumor spread, yet their precise contribution to metastasis is currently unclear (Pollard, "Tumor-educated Macrophages Promote Tumor Progression and Metastasis," *Nat. Rev. Cancer.* 4:71-78 (2004) and Hiratsuka et al., "MMP9 Induction by Vascular Endothelial Growth Factor Receptor-1 is Involved in Lung-specific Metastasis," *Cancer Cell.* 2:289-300 (2002)).

The present invention is directed to utilizing these phenomena in monitoring and treating cancer and metastasis.

SUMMARY OF THE INVENTION

The present invention is directed to a method of inhibiting tumor formation in a cancer patient at a site remote from sites of prior tumor formation. This method involves administering to the cancer patient an inhibitor of vascular endothelial growth factor receptor 1+ bone marrow-derived cells under conditions effective to inhibit tumor formation in the cancer patient at a site remote from sites of prior tumor formation.

A further aspect of the present invention is directed to a method of preventing metastases in a cancer patient. This method involves administering to the cancer patient an inhibitor of vascular endothelial growth factor receptor 1+ bone marrow-derived cells under conditions effective to prevent metastases in the cancer patient.

Another aspect of the present invention is directed to a method of identifying candidate compounds useful in inhibiting tumor formation or preventing metastases in a cancer patient. This involves providing a test compound and incubating the test compound with vascular endothelial growth factor receptor 1+ bone marrow-derived cells. Test compounds which bind to vascular endothelial growth factor receptor 1+ bone marrow-derived cells are identified as candidate compounds useful in inhibiting tumor formation or preventing metastases in a cancer patient.

An another aspect of the present invention relates to a method of monitoring metastases in a cancer patient. This method involves evaluating a patient sample for level of vascular endothelial growth factor receptor 1+ bone marrow-derived cells and comparing the level of vascular endothelial growth factor receptor 1+ bone marrow-derived cells to prior levels of vascular endothelial growth factor receptor 1+ bone marrow-derived cells, where an increase in the level of vascular endothelial growth factor receptor 1+ bone marrow-derived cells is indicative of future metastases.

A further aspect of the present invention relates to a method of inhibiting fibronectin expression in a subject at a site remote from sites of prior tumor formation. This involves administering to the subject an inhibitor of vascular endothelial growth factor receptor 1+ bone marrow-derived cells under conditions effective to inhibit fibronectin expression in the subject at a site remote from sites of prior tumor formation.

At present, it is very difficult to determine those patients with solid tumors after complete resection or partial resection and adjuvant chemotherapy that will then develop metastasis. The system of measuring VEGFR1+ bone marrow derived cells in frequent sites of metastasis for any given tumor (for example liver in colon cancer patients, lung in osteosarcoma patients, lymph node in breast cancer patients) can serve to help predict which patients will require additional adjuvant treatment targeted against these VEGFR1+ bone marrow derived clusters as well as more conventional therapy for example upfront treatment after resection with chemotherapy rather than waiting for the presentation of metastatic or recurrent disease. These cellular clusters which may also be tracked in the bloodstream as circulating or mobilized cells expressing VEGFR1 or VLA. In addition, it is possible in the future that these VEGFR1+ hematopoietic progenitor cells may be tagged so as to be followed by imaging studies to follow response to therapy or to assess future metastatic risk. It can serve to change the approach to staging and monitoring for minimal residual disease. Such a marker and potential treatment strategy should prove to be very useful for the care of patients with a primary tumor as well as those patients. It is foreseeable that this strategy may also work for those patients with ischemic disease and inflammatory illnesses such as rheumatoid arthritis and inflammatory bowel disease.

In the presence of these VEGFR1+ bone marrow-derived cells in sites of metastasis prior to tumor spread leading to the formation of a conducive microenvironment for incoming VEGFR2+ endothelial cells and tumor cells provides evidence that these cells produce a novel chemokine or growth factor which can explain these characteristics. The isolation/identification of novel proteins/genes involved in VEGFR1+ cells and the pre-metastatic niche causing enhanced tumor cell migration and adherence will provide an important target for the prevention of tumor spread.

BRIEF DESCRIPTION OF THE DRAWINGS

In FIG. 1A, β-gal+ bone marrow cells (left panel) are rarely observed in lungs after irradiation and before LLC cell implantation (n=6). By day 14, β-gal+ bone marrow-derived clusters appear in the lung parenchyma (left middle panel and magnified inset of the region arrowed; n=25) and are associated with micrometastases by day 23 (right panel, arrows) and in gross metastases (right panel, inset; n=12). Also shown is a cluster with associated stroma between a terminal bronchiole and bronchial vein, a common metastatic site (right middle panel). B is a terminal bronchiole, and V is a bronchial vein. FIG. 1B shows GFP+ bone marrow in the lungs after irradiation and before DsRed-tagged B16 cell implantation (left panel; n=6). On day 14, GFP+ BMDCs are seen with no DsRed+ tumor cells (left middle panel and inset; n=12). Beginning on day 18, a few single DsRed+ B16 cells adhere to GFP+ bone marrow clusters (right middle panel), and, by day 23, DsRed+ tumor cells proliferate at cluster sites (right panel; n=8). DAPI stain shows cell nuclei. FIG. 1C is a graph showing flow cytometric data of bone marrow-derived GFP+ BMDCs and DsRed+ B16 cells in the lung (n=30), and two flow diagrams on day 14 (left panel) and day 18 (right panel). FIG. 1D shows GFP+ BMDCs mobilized with B16 conditioned media, then DsRed-tagged tumor cells injected through the tail vein adhere 24 h later (right panel, arrows) compared with animals receiving media alone (left panel; P<0.01). Inset shows proliferating tumor cells in a cluster after four days (right panel inset; n=6). FIG. 1E shows a number of clusters per 100× objective field in animals with intradermal LLC or B16 tumors (n=12). Scale bar at bottom right applies for FIG. 1A (left, left middle, right middle, 80 mm; left middle inset, 8 mm; right, 20 mm; right inset, 47 mm), for FIG. 1B (left, left middle, 80 mm; left middle inset, 8 mm; right middle, right, 40 mm), and for FIG. 1D (40 mm; right inset, 20 mm). Pre-metastatic clusters are comprised of VEGFR1+ haemato-poietic progenitors. FIG. 1F shows VEGFR1 staining in irradiated lung before tumor implantation (left panel and inset; n=10) and 14 days after LLC cell implantation showing clusters in the lung (right panel, arrows; n=18, 3.9±0.2% cells with VEGFR1 staining per 100× objective field, P<0.05). FIGS. 1G and H show double immunofluorescence in the lung of an animal with day 14 LLC tumor. VEGFR1+ and GFP+ bone marrow cells (left panel), VEGFR1+ and CD133+ (right panel) are shown in FIG. 1G. VEGFR1+ and CD117+ are shown in FIG. 1H. FIG. 1I shows VEGFR1+ clusters in c-Myc transgenic lymph node at day 40 of life and before tumorigenesis (middle panel and inset showing VEGFR1+ cells) as compared with wild-type littermate lymph node without the transgene (left panel), and day 120 c-Myc transgenic node with lymphomas (right panel). In the inset of the right panel, arrows indicate the VEGFR1+ clusters surrounded by lymphoma (n=6). Scale bar at bottom right applies to FIG. 1E (80 mm; left inset, 40 mm), FIG. 1G (20 mm), FIG. 1H (20 mm), and FIG. 1I (80 mm; insets, 8 mm).

FIGS. 2A-B show inhibition of homing of bone marrow cells prevents metastasis. FIG. 2A shows VEGFR1+-selected bone marrow (R1-pos) permits micrometastasis (arrows, middle panel) but prevents well-vascularized large metastases as seen in wild types (left panel), 24 days after LLC implantation. Insets show CD31 (endothelial marker) expression. Bone marrow depleted of VEGFR1+ cells (non-R1) abrogates both clusters and metastases (right panel) (P<0.01 by ANOVA). The table shows the number of clusters and micrometastases per 100× objective field. * denotes that the metastasis filled the lung. (R1-pos, n=4; non-R1, n=4; wild type, n=6; non-R1 plus wild type, n=4). FIG. 2B shows treatment with antibodies to VEGFR1 (anti-R1) and VEGFR2 (anti-R2) in mice with LLC tumors prevents both clusters and metastases (P<0.01 by ANOVA; for all groups, n=5). Arrows in the lung of the wild type denote a large LLC metastasis. Arrows in anti-R2 show a cluster, inset shows a micrometastasis within a cluster. T, tumor cells. The table shows the number of clusters and LLC micrometastases in lung per 100× objective field. * denotes that the metastasis filled the tissue. Scale bar at bottom right applies to FIG. 2A (20 mm; wild type inset, 26 mm; R1-pos inset, 32 mm) and FIG. 2B (40 mm; anti-R2 inset, 20 mm).

FIGS. 3A-F show the VLA4/fibronectin pathway mediates cluster formation. FIGS. 3A-C show wild-type mice 14 days after tumor implantation develop clusters expressing VLA-4 (inset, VEGFR1 and VLA-4), MMP9 and Id3 (inset, VEGFR1 and Id3). FIG. 3D shows lung tissue in Id3 knock-out (KO) mice with LLC tumors given VEGFR1+ GFP+ BMDCs (P<0.01 by ANOVA; n=6). Arrows show region in upper inset. Arrows (lower inset) show the site of metastasis with GFP+VEGFR1+ cells. FIG. 3E shows baseline fibronectin expression in the wild-type lung (n=6) (left panel). Increased stromal fibronectin in the peribronchial region of the pre-metastatic lung at day three (middle panel, arrows), with maximal expression on day 14 (right panel). Insets, PDGFRα expression indicates resident fibroblasts laying down fibronectin. FIG. 3F shows quantitative RT-PCR reveals increased fibronectin expression in the lungs of mice with LLC tumors compared with wild type (*P<0.05 by ANOVA; n=6), and a similar earlier trend in lungs from animals with B16 melanoma. Scale bar at top right applies to FIGS. 3A-C (40 mm; insets, 8 mm), FIG. 3D (80 mm; top right inset, 20 mm; bottom right inset 80 mm) and FIG. 3E (40 mm; insets, 20 mm).

FIGS. 4A-B show that by quantitative RT-PCR analysis, increased fibronectin expression was seen in the oviduct (FIG. 4A) and intestine (FIG. 4B) in mice given MCM compared with wildtype and LCM-treatment. For oviduct, *P<0.05 at days 3-5 and **P<0.001 for days 7-9 compared with wild type, and for intestine, *P<0.001 at days 7-9 compared with wild type by ANOVA (n=6). FIG. 4C shows an ELISA assay (in triplicate) for VEGF and PlGF levels in the conditioned media (*P<0.05 when compared with L-LCM, P<0.01 when compared with media alone, by ANOVA). FIG. 4D shows transwell migration assays (in triplicate) demonstrate enhanced migration of VEGFR1+ cells to LCM and MCM (P<0.001 by ANOVA). FIG. 4E shows treatment with MCM redirects the metastatic spread of LLC to B16 melanoma metastatic sites, such as the spleen (left panel), kidney (left middle panel), intestine (right middle panel) and oviduct (right panel). Arrows denote the regions of metastatic borders, which are shown in the insets (n=6). T, LLC tumor cells. Scale bar at bottom right applies to FIG. 4E (200 mm; inset, 20 mm).

FIG. 5A shows flow cytometric analysis of day 8, 14, 18, and 23, delineating the populations of GFP+ BMDCs and DsRed B16 Melanoma tumor cells in the lung (n=30). FIG. 5B shows VEGFR1 with CD34 (middle panel) frequency of co-expression of VEGFR1 and these hematopoietic markers (right graph). FIG. 5C shows analysis of CD117+ progenitor cells and fluorescent GFP+-LLC tumor cells in the lung by flow cytometry reveals the presence of these cells prior to tumor cell arrival represented by day 12, 14, 18, and 27. FIG. 5D shows bone marrow derived VEGFR2+ circulating endothelial progenitors arrive at the premetastatic niche after the VEGFR1+ hematopoietic progenitors. Double immunofluorescence of VEGFR1 with VEGFR2 (left panel). VEGFR1 with CD31/PECAM (middle panel) (arrows indicate endothelial cells). Double immunofluorescence of VEGFR2+ cells with GFP signify bone marrow origin of these cells within the established and growing metastatic niche (right panel). FIG. 5E is a graph illustrates timing of arrival of VEGFR-2+ cells to the metastatic niche which coincides with tumor cell arrival as seen in lung tissue from animals with day 16 and day 24 tumors (cells/cluster/

Figure 5A:
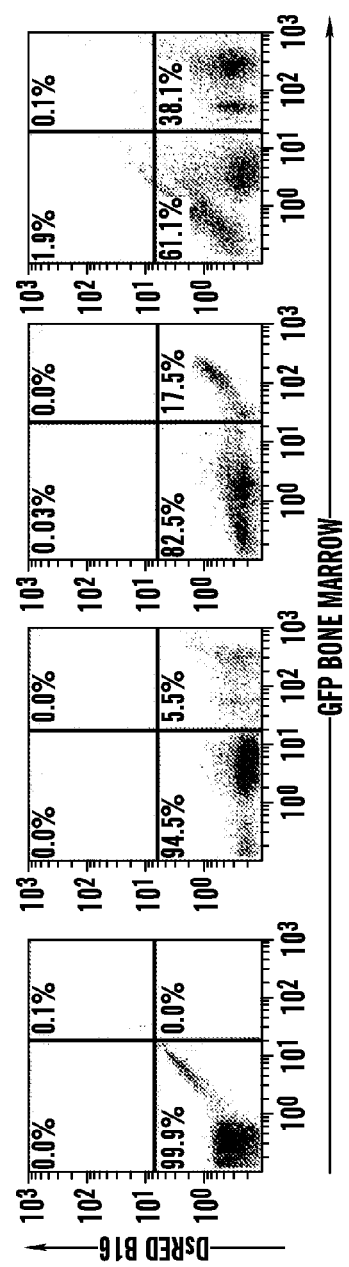
FIGS. 5A-E show tumor and VEGFR2+ cells arrive after VEGFR1+ HPCs.
Figure 5B:
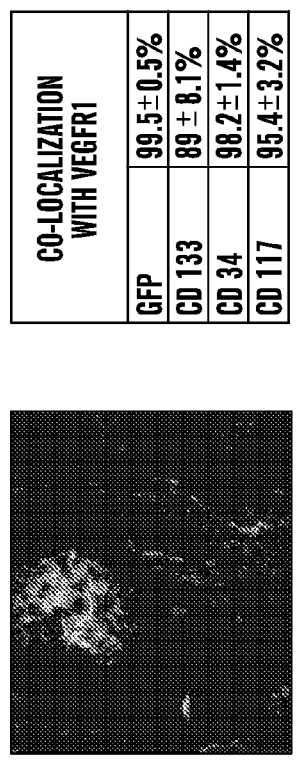
Figure 5C:
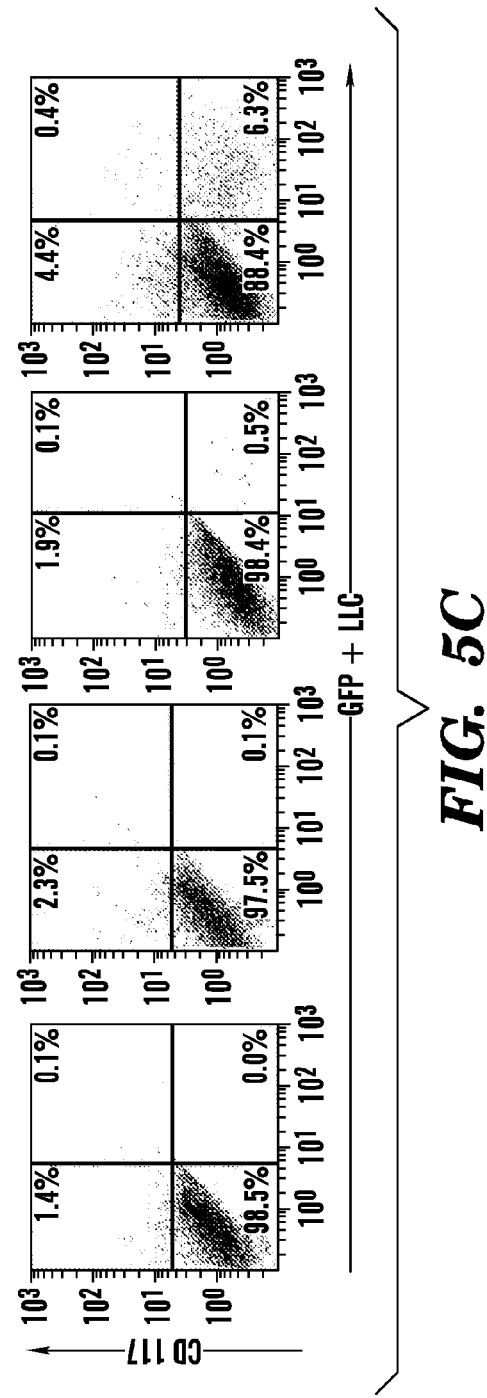
Figure 5D:
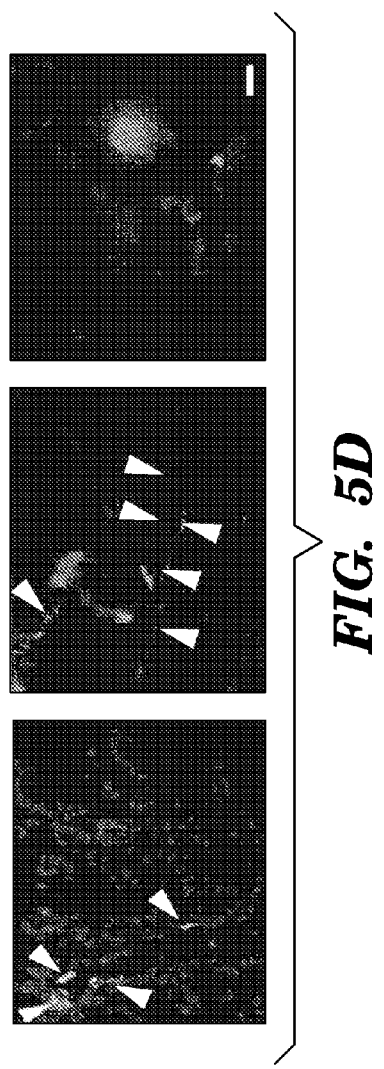
Figure 5E:
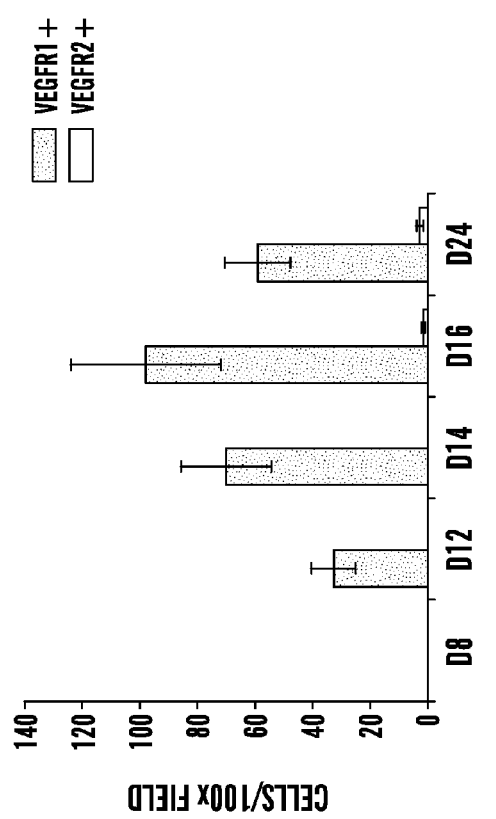

100× field) (n=6). Scale bars: 20 μm (FIG. 5B); left, middle left 20 μm, right 10 μm (FIG. 5D).

Figure 6A:
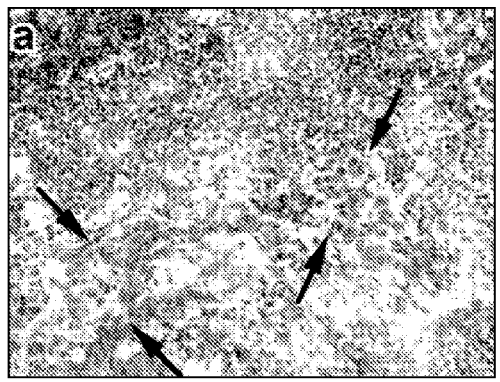
Figure 6B:
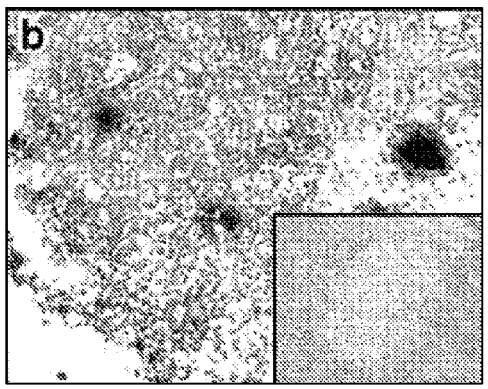
Figure 6C:
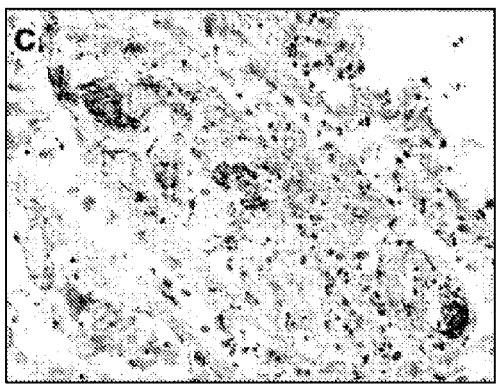
Figure 6D:
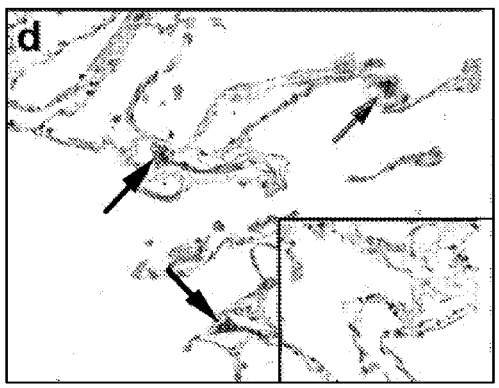
Figure 6E:
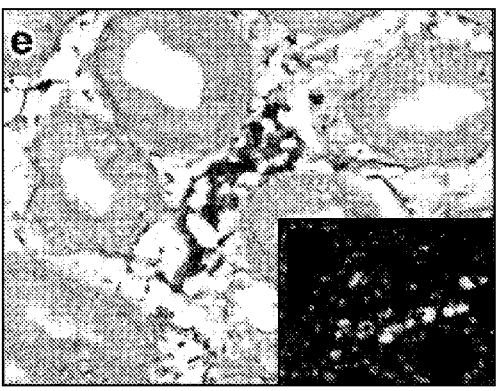
Figure 6F:
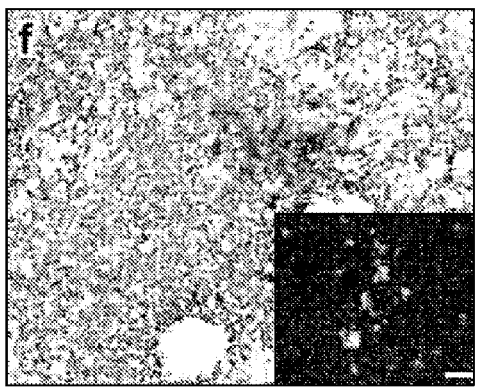

FIGS. 6A-F show expression of VEGFR1 in pre-metastatic human tissue. Cellular clusters were stained with VEGFR1 in malignant and non-malignant tissues in individuals with breast (n=15), lung (n=15) and gastrointestinal (n=3) cancers. FIG. 6A shows lymph nodes with evidence of breast adenocarcinoma metastasis (arrows indicate tumor), while FIG. 6B shows the lymph node without malignancy from same patient. FIG. 6C shows primary lung adenocarcinoma, while FIG. 6D shows adjacent 'normal' lung without neoplasm (arrows indicate VEGFR1$^+$ cells). No VEGFR1$^+$ clusters were seen in lymph node (FIG. 6B inset; n=6) and lung tissue (FIG. 6D inset; n=3) from individuals without cancer. Also shown is a primary adenosquamous carcinoma of the gastroesophageal junction (FIG. 6E) and a hepatic lymph node without carcinoma (FIG. 6F). The insets in FIGS. 6E-F show co-immunofluorescence of VEGFR1 and c-Kit. Scale bar at bottom right applies to all panels (40 mm; insets, 40 mm).

Figure 7C:
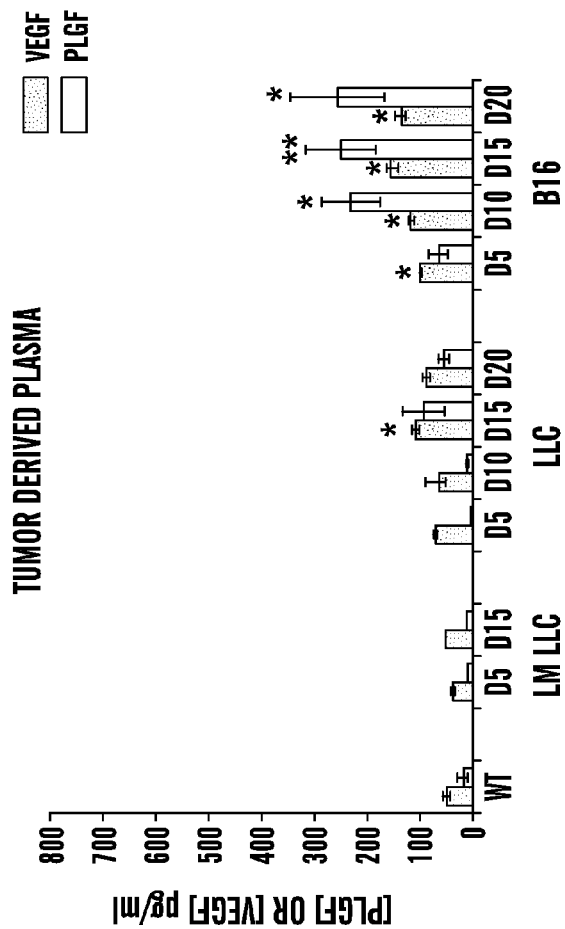

FIGS. 7A-C show tumors vary in their chemokine profile and fibronectin expression pattern. FIG. 7A shows WT mice treated with LLC conditioned media (LCM) induce fibronectin expression in the liver (left panel) and lung (middle panel) compared to media controls (left and middle panel insets) (n=12). LCM supports β-gal$^+$ BM clusters in the lung (right panel, TB=terminal bronchiole and BV=bronchial vein) (n=6). FIG. 7B shows mice treated with MCM develop enhanced fibronectin expression in the liver (left panel) and intestine (middle panel) as well as kidney, testis, and lung with media control for fibronectin expression in intestine (middle panel inset) (n=12). WT mice with β-gal$^+$ BM treated with MCM exhibit adjacent cluster formation localizing to the fibronectin enriched areas. (right panel) (n=6). FIG. 6C shows ELISA levels for VEGF and PlGF in tumor-derived plasma for both LLC and B16 melanoma obtained from animals with day 14 tumor (in triplicates *p<0.05 for tumor-derived plasma compared to WT plasma, by one way ANOVA). The scale bars for FIGS. 7A-B are: left and middle panels 40 μm, insets 35.2 μm, right panel 20 μm.

Figure 8A:
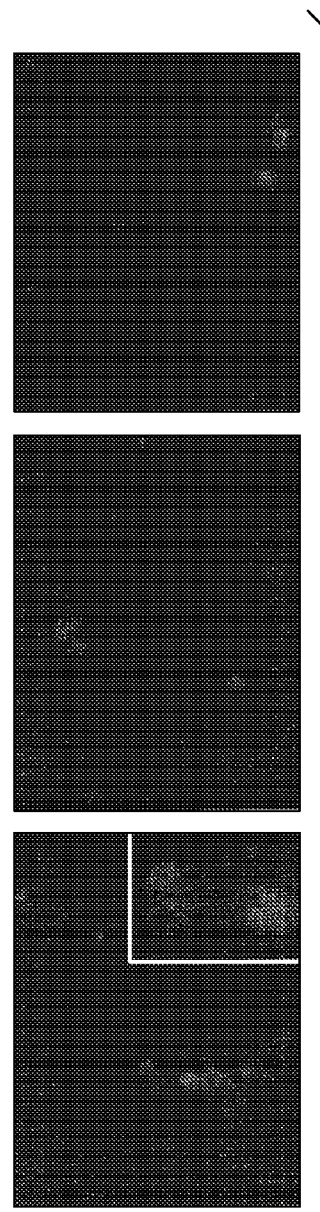
Figure 8B:
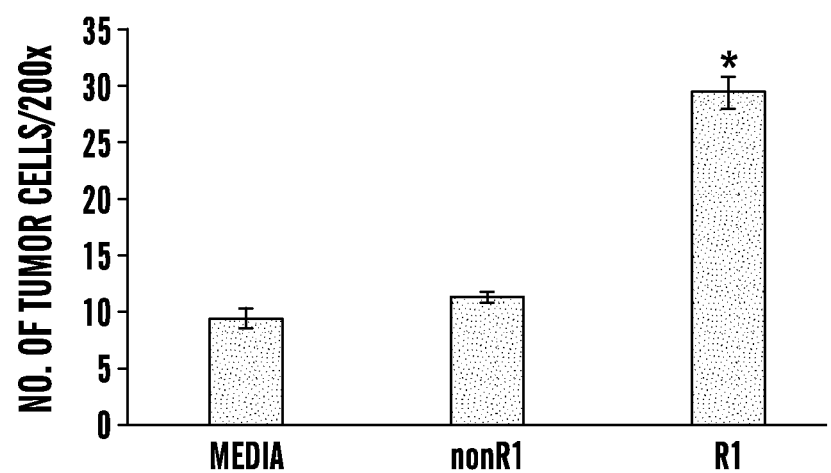
Figure 8C:
Figure 8D:
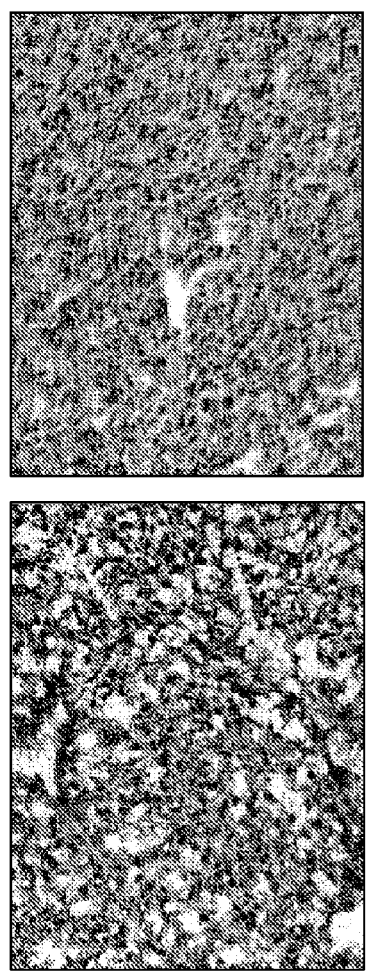

FIGS. 8A-D show bone marrow-derived VEGFR1$^+$ cells attract tumor cells. FIG. 8A shows VEGFR1$^+$ cells isolated from BM and co-cultured with B16 tumor cells form aggregates and proliferate, with this effect being lost with antibody treatment to VEGFR1 (middle panel) or VLA-4 (right panel). FIG. 8B shows transwell migration assay demonstrate increased migration of B16 tumor cells to VEGFR1$^+$ selected population (in triplicates, p<0.001% for R1 compared to non R1 and media). FIG. 8C shows SDF-1 (CXCL12) immunofluorescent staining of a VEGFR1$^+$ cellular cluster at low and high magnification. Co-immunofluorescence of SDF-1α and VEGFR1 with VEGFR1$^+$ cellular clusters staining positive for SDF-1α expression. FIG. 8D shows LLC and B16 tumor cells express CXCR4. Scale bars: 50 μm, inset 120 μm for FIG. 8A, left and right panel 40 μm, middle 8 μm for FIG. 8C, and 20 μm for FIG. 8D.

Figure 9:
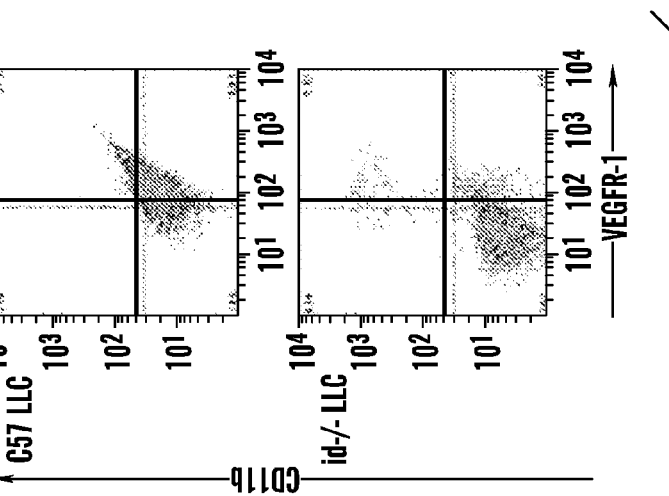

FIG. 9 shows that Id3 knockout mice lack HPC mobilization, and that Id3 deficient mice have decreased mobilization of CD11b$^+$ VEGFR1$^+$ hematopoietic progenitors.

Figure 10:
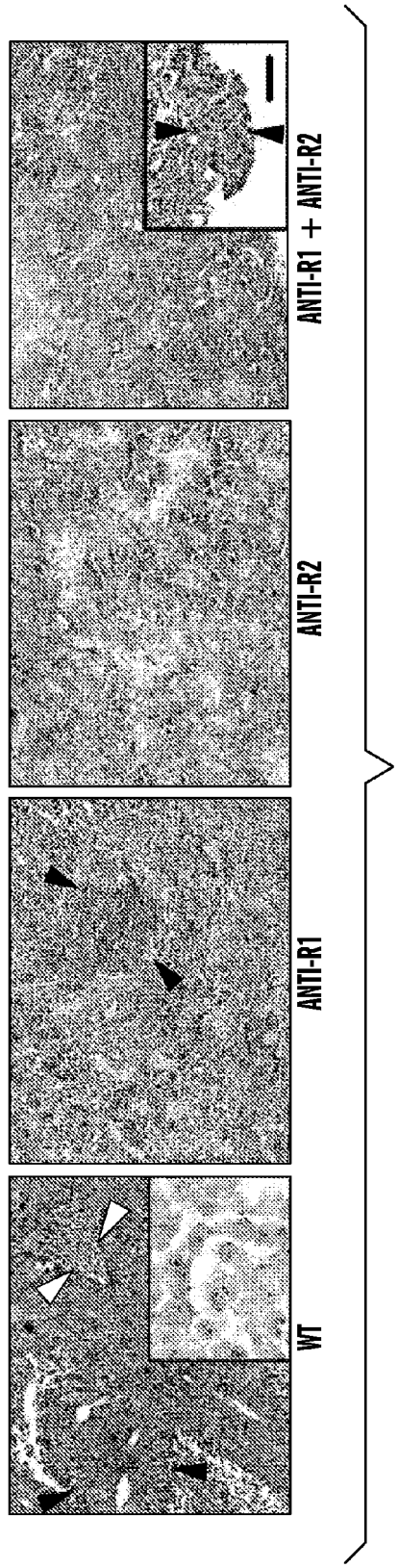

FIG. 10 shows VEGFR1 antibody inhibits metastasis in B16 tumors. B16 tumors (right panels) are shown in mice treated with neutralizing antibody to VEGFR1 and/or VEGFR2. The closed arrows in spleen of WT show viable melanoma along with inset, while the open arrows reveal necrosis and melanin granules. The arrows in anti-R1 (anti-VEGFR1) show a typical germinal center in spleen. The inset in anti-R1+anti-R2 group represents isolated metastasis in the lung of one animal. The scale bars are: 20 μm: insets WT spleen 8 μm, anti-R1+anti-R2 66 μm.

Figure 11A:
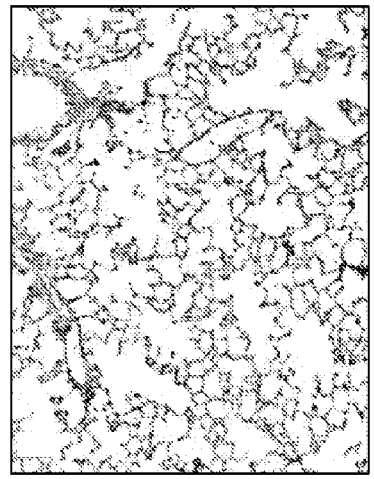
Figure 11B:
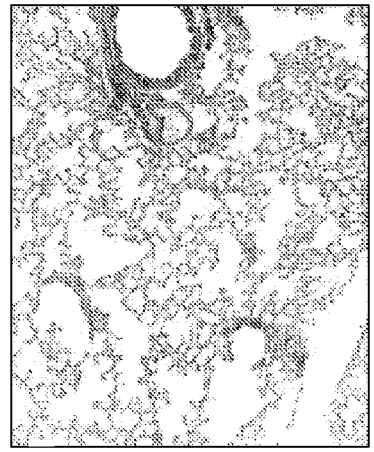
Figures 11C, 11D:
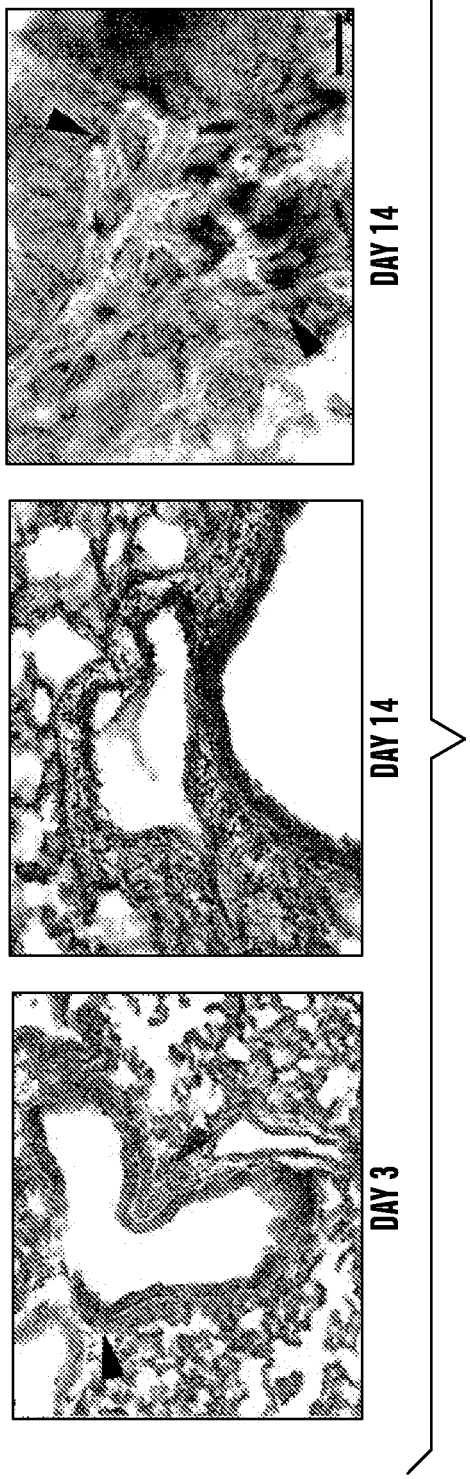

FIGS. 11A-D show that inhibition of VLA-4 and MMP-9 inhibits metastasis. B16 melanoma induces fibronectin expression in the lung. Images represent lung tissue 14 days after LLC implantation in WT mice treated with anti-VLA-4 antibodies (β-gal with eosin counterstain, n=8, p<0.01 by Student's t test) (FIG. 11A) and MMP9$^{-/-}$ mice (VEGFR1 DAB with haematoxylin counterstain n=6) (FIG. 11B). The WT mice given VLA-4 antibodies or in MMP-9 deficient mice have reduced β-gal and VEGFR1 cellular cluster formation represented in FIG. 11C below images quantifying clusters or metastasis/100× field (p<0.01 by Student's t test). FIG. 11D shows fibronectin expression in lung tissue at days 3 and 14 after B16 melanoma tumor implantation. Arrows in day 14 represent fibronectin expression in a cluster site. The scale bars are: 80 μm (FIG. 11A), and left, middle panels 40 μm, right 8 μm (FIG. 11D).

DETAILED DESCRIPTION OF THE INVENTION

The present invention is directed to a method of inhibiting tumor formation in a cancer patient at a site remote from sites of prior tumor formation. This method involves administering to the cancer patient an inhibitor of vascular endothelial growth factor receptor 1$^+$ bone marrow-derived cells under conditions effective to inhibit tumor formation in the cancer patient at a site remote from sites of prior tumor formation. This inhibitor can also be used to prevent tumor recurrence at the primary tumor site.

The administering step of this method is carried out at a time period corresponding to when vascular endothelial growth factor receptor 1$^+$ bone marrow-derived cell mobilization is stimulated. Such stimulation can occur as a result of chemotherapy, stress, surgery, bone marrow recovery in a cancer patient, inflammation, irradiation, or growth factors. In stimulating growth factors, such as granulocyte colony stimulating factors, granulocyte macrophage stimulating factors, and erythropoietin, the mobilization of hematopoietic cells in the bloodstream may be stimulated and tumor growth and metastasis promoted.

In carrying out the present invention, the inhibitors of vascular endothelial growth factor receptor 1$^+$ bone marrow-derived cells are selected to bind to vascular endothelial growth factor receptor 1$^+$ bone marrow-derived cells.

The inhibitor of vascular endothelial growth factor receptor 1$^+$ bone marrow-derived cells is selected to prevent or reduce formation of vascular endothelial growth factor receptor 1$^+$ bone marrow-derived cells. Suitable inhibitors can be a vascular endothelial growth factor receptor 1$^+$ bone marrow-derived cell-specific biological molecules or small molecules that inhibit RNA or DNA.

Biological molecules include all lipids and polymers of monosaccharides, amino acids, and nucleotides having a molecular weight greater than 450. Thus, biological molecules include, for example, oligosaccharides and polysaccharides oligopeptides, polypeptides, peptides, and proteins; and oligonucleotides and polynucleotides. Oligonucleotides and polynucleotides include, for example, DNA and RNA.

Biological molecules further include derivatives of any of the molecules described above. For example, derivatives of biological molecules include lipid and glycosylation derivatives of oligopeptides, polypeptides, peptides and proteins. Derivatives of biological molecules further include lipid derivatives of oligosaccharides and polysaccharides, e.g. lipopolysaccharides.

Most typically, biological molecules are vascular endothelial growth factor receptor 1+ bone marrow-derived cell-specific antibodies, or functional equivalents of such antibodies. Such functional equivalents include, for example, chimerized, humanized, and single chain antibodies as well as fragments thereof.

The functional equivalent of an antibody is preferably a chimerized or humanized antibody. A chimerized antibody comprises the variable region of non-human antibody and the constant region of a human antibody. A humanized antibody comprises the hypervariable region (CDRs) of a non-human antibody. The variable region other than the hypervariable region, e.g. the framework variable region, and the constant region of a humanized antibody are those of a human antibody.

For the purposes of this application, suitable variable and hypervariable regions of non-human antibodies may be derived from antibodies produced by any non-human mammal in which monoclonal antibodies are made. Suitable examples of mammals other than humans include, for example, rabbits, rats, mice, horses, goats, or primates. Mice are preferred.

Functional equivalents further include fragments of antibodies that have binding characteristics that are the same as, or are comparable to, those of the whole antibody.

Such fragments may, for example, contain one or both Fab fragments of the $F(ab')_2$ fragment. Preferably, the antibody fragments contain all six complementarity determining regions of the whole antibody, although functional fragments containing fewer than all of such regions, such as three, four or five CDRs, are also included.

The preferred fragments are single chain antibodies, or Fv fragments. Single chain antibodies are polypeptides that comprise at least the variable region of the heavy chain of the antibody linked to the variable region of the light chain, with or without an interconnecting linker. Thus, Fv fragment comprises the entire antibody combining site. These chains may be produced in bacteria or in eukaryotic cells.

The antibodies and functional equivalents may be members of any class of immunoglobulins, such as: IgG, IgM, IgA, IgD, or IgE, and the subclasses thereof. The preferred antibodies are members of the IgG1 subclass. The functional equivalents may also be equivalents of combinations of any of the above classes and subclasses.

Antibodies of the present invention are capable of binding vascular endothelial growth factor receptor 1+ bone marrow-derived cells and may function to inhibit the activity of such. Such antibodies may have therapeutic potential, particularly in the treatment of cancer by inhibiting the function of vascular endothelial growth factor receptor 1+ bone marrow-derived cells.

Antibodies of the present invention are capable of binding VLA-4 ($\alpha 4\beta 1$) integrin, inhibiting formation of these bone marrow derived clusters. Such antibodies may have therapeutic potential, particularly in the treatment of cancer by inhibiting the function of VEGFR1+ and VLA-4+ bone marrow derived cells.

Antibodies of the present invention may be either monoclonal antibodies or polyclonal antibodies.

Monoclonal antibody production may be carried out by techniques which are well-known in the art. In overview, the process involves first obtaining immune cells (lymphocytes) from the spleen of a mammal (e.g., mouse) which has been previously immunized with the antigen of interest either in vivo or in vitro. The antibody-secreting lymphocytes are then fused with (mouse) myeloma cells or transformed cells, which are capable of replicating indefinitely in cell culture, thereby producing an immortal, immunoglobulin-secreting cell line. The resulting fused cells, or hybridomas, are cultured, and the resulting colonies screened for the production of the desired monoclonal antibodies. Colonies producing such antibodies are cloned, and grown either in vivo or in vitro to produce large quantities of antibody. A description of the theoretical basis and practical methodology of fusing such cells is set forth in Kohler et al., *Nature* 256:495 (1975), which is hereby incorporated by reference in its entirety.

Mammalian lymphocytes are immunized by in vivo immunization of the animal (e.g., a mouse) with the vascular endothelial growth factor receptor 1+. Such immunizations are repeated as necessary at intervals of up to several weeks to obtain a sufficient titer of antibodies. Following the last antigen boost, the animals are sacrificed and spleen cells removed.

Fusion with mammalian myeloma cells or other fusion partners capable of replicating indefinitely in cell culture is effected by standard and well-known techniques, for example, by using polyethylene glycol ("PEG") or other fusing agents (Milstein et al., *Eur. J. Immunol.* 6:511 (1976), which is hereby incorporated by reference in its entirety). This immortal cell line, which is preferably murine, but may also be derived from cells of other mammalian species, including but not limited to rats and humans, is selected to be deficient in enzymes necessary for the utilization of certain nutrients, to be capable of rapid growth, and to have good fusion capability. Many such cell lines are known to those skilled in the art, and others are regularly described.

Procedures for raising polyclonal antibodies are also well known. Typically, such antibodies can be raised by administering the vascular endothelial growth factor receptor 1+ subcutaneously to New Zealand white rabbits which have first been bled to obtain pre-immune serum. The antigens can be injected at a total volume of 100 µl per site at six different sites. Each injected material will contain synthetic surfactant adjuvant pluronic polyols, or pulverized acrylamide gel containing the protein or polypeptide after SDS-polyacrylamide gel electrophoresis. The rabbits are then bled two weeks after the first injection and periodically boosted with the same antigen three times every six weeks. A sample of serum is then collected 10 days after each boost. Polyclonal antibodies are then recovered from the serum by affinity chromatography using the corresponding antigen to capture the antibody. Ultimately, the rabbits are euthanized with pentobarbital 150 mg/Kg IV. This and other procedures for raising polyclonal antibodies are disclosed in Harlow et. al., editors, *Antibodies: A Laboratory Manual* (1988), which is hereby incorporated by reference in its entirety.

Antibodies that are essentially human may be produced in transgenic mammals, especially transgenic mice that are genetically modified to express human antibodies. Methods for making chimeric and humanized antibodies are also known in the art. For example, methods for making chimeric antibodies include those described in U.S. Pat. Nos. 4,816,397 and 4,816,567, which are hereby incorporated by reference in their entirety. Methods for making humanized antibodies are described in U.S. Pat. No. 5,225,539, which is hereby incorporated by reference in its entirety.

The preferred method for humanization of antibodies is called CDR-grafting. In CDR-grafting, the regions of the mouse antibody that are directly involved in binding to antigen, the complementarity determining region of CDRs, are grafted into human variable regions to create "reshaped human" variable regions. These fully humanized variable regions are then joined to human constant regions to create complete "fully humanized" antibodies.

In order to create fully humanized antibodies that bind well to an antigen, it is advantageous to design the reshaped human variable regions carefully. The human variable regions into which the CDRs will be grafted should be carefully selected, and it is usually necessary to make a few amino acid changes to critical positions within the framework regions (FRs) of the human variable regions.

For example, the reshaped human variable regions may include up to ten amino acid changes in the FRs of the selected human light chain variable region, and as many as twelve amino acid changes in the FRs of the selected human heavy chain variable region. The DNA sequences coding for these reshaped human heavy and light chain variable region genes are joined to DNA sequences coding for the human heavy and light chain constant region genes, preferably γ1 and κ, respectively. The reshaped humanized antibody is then expressed in mammalian cells and its affinity for its target compared with that of the corresponding murine antibody and chimeric antibody.

Methods for selecting the residues of the humanized antibody to be substituted and for making the substitutions are well known in the art. See, for example, Co et al., Nature 351:501-502 (1992); Queen et al., Proc. Natl. Acad. Sci. USA 86:10029-1003 (1989) and Rodrigues et al., Int. J. Cancer, Supplement 7:45-50 (1992), which are hereby incorporated by reference in their entirety. A method for humanizing and reshaping the 225 anti-EGFR monoclonal antibody is described by WO 96/40210, which is hereby incorporated by reference in its entirety. This method can be adapted to humanizing and reshaping antibodies against other proteins.

Methods for making single chain antibodies are also known in the art. Some examples include those described by European Patent Application No. 502 812 and Wels et al., Int. J. Cancer 60:137-144 (1995), which are hereby incorporated by reference in their entirety. Single chain antibodies may also be prepared by screening phage display libraries.

Other methods for producing the functional equivalents described above are disclosed in WO 93/21319, European Patent Application No. 239 400, WO 89/09622, European Patent Application No. 338 745, U.S. Pat. No. 5,658,570, U.S. Pat. No. 5,693,780, and European Patent Application No. 332 424, which are hereby incorporated by reference in their entirety.

In practicing the methods of the present invention, the administering step is carried out by administering the subject inhibitor, orally, intradermally, intramuscularly, intraperitoneally, intravenously, subcutaneously, or intranasally. The inhibitor of the present invention may be administered alone or with suitable pharmaceutical carriers, and can be in solid or liquid form, such as tablets, capsules, powders, solutions, suspensions, or emulsions.

The inhibitor of the present invention may be orally administered, for example, with an inert diluent, or with an assimilable edible carrier, or it may be enclosed in hard or soft shell capsules, or it may be compressed into tablets, or it may be incorporated directly with food. For oral therapeutic administration, the inhibitor of the present invention may be incorporated with excipients and used in the form of tablets, capsules, elixirs, suspensions, syrups, and the like. Such compositions and preparations should contain at least 0.1% of the inhibitor of the present invention. The percentage of the inhibitor in these compositions may, of course, be varied and may conveniently be between about 2% to about 60% of the weight of the unit. The amount of inhibitor of the present invention in such therapeutically useful compositions is such that a suitable dosage will be obtained.

The tablets, capsules, and the like may also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin. When the dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar, or both. A syrup may contain, in addition to active ingredient, sucrose as a sweetening agent, methyl and propylparabens as preservatives, a dye, and flavoring such as cherry or orange flavor.

The inhibitor of the present invention may also be administered parenterally. Solutions or suspensions of the inhibitor can be prepared in water suitably mixed with a surfactant such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

The inhibitors of the present invention may also be administered directly to the airways in the form of an aerosol. For use as aerosols, the inhibitor of the present invention in solution or suspension may be packaged in a pressurized aerosol container together with suitable propellants, for example, hydrocarbon propellants like propane, butane, or isobutane with conventional adjuvants. The inhibitor of the present invention also may be administered in a non-pressurized form, such as in a nebulizer or atomizer.

The present invention is useful in treating a wide variety of cancers. Treating cancer, as used herein, specifically refers to administering therapeutic agents to a patient diagnosed with cancer, i.e., having established cancer in the patient, to inhibit the further growth or spread of the malignant cells in the cancerous tissue, and/or to cause the death of the malignant cells. In particular, breast cancers, colon cancers, prostate cancers, lung cancers and skin cancers as well as many pediatric cancers may be amenable to the treatment by the methods of the present invention. Treating cancer also encompasses treating a patient having premalignant conditions to stop the progression of, or cause regression of, the premalignant conditions. Examples of premalignant conditions include hyperplasia, dysplasia, and metaplasia.

The therapeutics of the present invention can be used alone or in conjunction with other cancer therapies (e.g., chemotherapeutic agents, radiation, or combinations thereof).

Examples of chemotherapeutic agents include alkylating agents (e.g., nitrogen mustards, ethyleneimine compounds and alkyl sulphonates); antimetabolites (e.g., folic acid, purine or pyrimidine antagonists); mitotic inhibitors (e.g., vinca alkaloids and derivatives of podophyllotoxin, and cytotoxic antibiotics); and compounds that damage or interfere with DNA expression.

Particular examples of chemotherapeutic agents or chemotherapy include cisplatin, dacarbazine (DTIC), dactinomycin, mechlorethamine (nitrogen mustard), streptozocin, cyclophosphamide, carmustine (BCNU), lomustine (CCNU), doxorubicin (adriamycin), daunorubicin, procarbazine, mitomycin, cytarabine, etoposide, methotrexate, 5-fluorouracil, vinblastine, vincristine, bleomycin, paclitaxel (taxol), docetaxel (taxotere), aldesleukin, asparaginase, busulfan, carboplatin, cladribine, dacarbazine, floxuridine, fludarabine, hydroxyurea, ifosfamide, interferon alpha, leuprolide, magastrol, melphalan, mercaptopurine, oxaloplatin, plicamycin, mitotane, pegaspargase, pentostatin, pipobroman, plicamycin, streptozocin, tamoxifen, teniposide, testolactone, thioguanine, thiotepa, uracil mustard, vinorelbine, chlorambucil, taxol, and combinations thereof.

The inhibitors of the present invention can also be used in combination with radiation. The source of radiation can be either external or internal to the patient being treated. When the source is external to the patient, the therapy is known as external beam radiation therapy (EBRT). When the source of radiation is internal to the patient, the treatment is called brachytherapy (BT).

The radiation is administered in accordance with well known standard techniques with standard equipment manufactured for this purpose, such as AECL Theratron and Varian Clinac. The dose of radiation depends on numerous factors as is well known in the art. Such factors include the organ being treated, the healthy organs in the path of the radiation that might inadvertently be adversely affected, the tolerance of the patient for radiation therapy, and the area of the body in need of treatment. The dose will typically be between 1 and 100 Gy, and more particularly between 2 and 80 Gy. Some doses that have been reported include 35 Gy to the spinal cord, 15 Gy to the kidneys, 20 Gy to the liver, and 65-80 Gy to the prostate. It should be emphasized, however, that the present invention is not limited to any particular dose. The dose will be determined by the treating physician in accordance with the particular factors in a given situation, including the factors mentioned above.

The distance between the source of the external radiation and the point of entry into the patient may be any distance that represents an acceptable balance between killing target cells and minimizing side effects. Typically, the source of the external radiation is between 70 and 100 cm from the point of entry into the patient.

Brachytherapy is generally carried out by placing the source of radiation in the patient. Typically, the source of radiation is placed approximately 0-3 cm from the tissue being treated. Known techniques include interstitial, intercavitary, and surface brachytherapy. The radioactive seeds can be implanted permanently or temporarily. Some typical radioactive atoms that have been used in permanent implants include iodine-125 and radon. Some typical radioactive atoms that have been used in temporary implants include radium, cesium-137, and iridium-192. Some additional radioactive atoms that have been used in brachytherapy include americium-241 and gold-198.

The dose of radiation for brachytherapy can be the same as that mentioned above for external beam radiation therapy. In addition to the factors mentioned above for determining the dose of external beam radiation therapy, the nature of the radioactive atom used is also taken into account in determining the dose of brachytherapy.

The particularly preferred embodiment of the present invention involves its use in conjunction with an adjuvant therapy regimen. In particular, this involves chemotherapy and the use of additional monoclonal antibodies to VEGFR1 and/or VLA-4 prior to and/or after surgery as well as throughout conventional adjuvant chemotherapy course or with primary chemotherapy (not adjuvant) course with no surgery. In addition, the present invention may be used to treat patients after primary surgery who may not otherwise receive treatment i.e. those patients with primary complete resection without evidence of residual or distant disease in order to prevent metastatic spread. Furthermore, the present invention may be used as a diagnostic tool as well to determine those patients at highest risk for metastatic spread.

A further aspect of the present invention is directed to a method of preventing metastases in a cancer patient. This method involves administering to the cancer patient an inhibitor of vascular endothelial growth factor receptor $1^+$ bone marrow-derived cells under conditions effective to prevent metastases in the cancer patient. This aspect of the present invention involves using substantially the same therapeutics and manner of treatment as described above.

In carrying out this aspect of the present invention, the inhibitor prevents or reduces formation or proliferation of vascular endothelial growth factor receptor $1^+$ bone marrow-derived cells. Such inhibitors may also prevent the migration of such cells or the formation or proliferation of tumors at other sites.

Another aspect of the present invention is directed to a method of identifying candidate compounds useful in inhibiting tumor formation or preventing metastases in a cancer patient. This involves providing a test compound and incubating the test compound with vascular endothelial growth factor receptor $1^+$ bone marrow-derived cells. Test compounds which bind to vascular endothelial growth factor receptor $1^+$ bone marrow-derived cells are identified as candidate compounds useful in inhibiting tumor formation or preventing metastases in a cancer patient.

Another aspect of the present invention relates to a method of monitoring metastases in a cancer patient. This method involves evaluating a patient sample for level of vascular endothelial growth factor receptor $1^+$ bone marrow-derived cells and comparing the level of vascular endothelial growth factor receptor $1^+$ bone marrow-derived cells to other levels of vascular endothelial growth factor receptor $1^+$ bone marrow-derived cells. Such other levels can be prior levels in the patient, where an increase in the level of vascular endothelial growth factor receptor $1^+$ bone marrow-derived cells is indicative of future metastases. Alternatively, the other level can be a standard or normal level, where the measurement of a level higher than the normal or standard may be indicative of metastases.

In carrying out this aspect of the present invention, the patient sample can be a tissue sample or a blood sample.

It is particularly desirable to carry out this aspect of the present invention by administering a therapeutic agent based on the step of comparing the level of vascular endothelial growth factor receptor $1^+$ bone marrow-derived cells to prior levels of vascular endothelial growth factor receptor $1^+$ bone marrow-derived cells. Such administration includes an adjuvant therapy regimen, as described above. Alternatively, the therapeutic agent can be a chemotherapeutic agent whose strength is selected based on comparing the level of vascular endothelial growth factor receptor $1^+$ bone marrow-derived cells to prior levels of vascular endothelial growth factor receptor 1+ bone marrow-derived cells.

This method can be carried out in vitro or in vivo. For the in vivo aspect of the present invention, the evaluating and comparing steps involve imaging an area in the cancer patient. This can be achieved using a labeling agent specific for vascular endothelial growth factor receptor 1+ bone marrow-derived cells or labeled vascular endothelial growth factor receptor 1+ bone marrow-derived cells, either of which is introduced into the cancer patient.

A further aspect of the present invention relates to a method of inhibiting fibronectin expression in a subject at a site remote from sites of prior tumor formation. This involves administering to the subject an inhibitor of vascular endothelial growth factor receptor 1+ bone marrow-derived cells under conditions effective to inhibit fibronectin expression in the subject at a site remote from sites of prior tumor formation. This aspect of the present invention involves using substantially the same therapeutics and manner of treatment as described above.

EXAMPLES

Example 1

Bone Marrow BM Transplantation

Wild-type C57Bl/6 mice were lethally irradiated (950 rads) and transplanted with $1 \times 10^6$ β-galactosidase+ or GFP+ BM cells (Rosa-26 mice) (Lyden et al., "Impaired Recruitment of Bone-marrow-derived Endothelial and Hematopoietic Precursor Cells Blocks Tumor Angiogenesis and Growth," *Nat. Med.* 7:1194-1201 (2001), which is hereby incorporated by reference in its entirety). After 4 weeks, mice were injected intradermally with either $2 \times 10^6$ LLC (ATCC) or B-16 cells (ATCC).

Example 2

β-Galactosidase Staining

Tissues and femoral bones were fixed in 4% paraformaldehyde (PFA) for 4 h. The samples were stained in X-gal solution at 37° C. for 36 hours, as described in Tam et al., "The Allocation of Epiblast Cells to the Embryonic Heart and other Mesodermal Lineages The Role of Ingression and Tissue Movement during Gastrulation," *Development.* 124:1631-1642 (1999), which is hereby incorporated by reference in its entirety. The X-gal stained tumors and BM were embedded as described in Lyden et al., "Impaired Recruitment of Bone-marrow-derived Endothelial and Hematopoietic Precursor Cells Blocks Tumor Angiogenesis and Growth," *Nat. Med.* 7:1194-1201 (2001), which is hereby incorporated by reference in its entirety.

Example 3

Fluorescent Tumor Transfection

B16 and LLC cells ($2 \times 10^5$) were plated 24 hours prior to transfection. Cells were then pelleted and resuspended into serum free media with lentiviral vector supernatant containing the DsRed reporter gene or GFP gene. Concentrated viral constructs with titers of $1-2 \times 10^8$ infectious particles per ml were used to infect $2 \times 10^6$ cells in a 1 ml (multiplicity of infection is 50) as previously described. Flow cytometric analysis was performed to confirm degree of fluorescence. C57Bl/6 mice were inoculated with $2 \times 10^6$ LLC/GFP+ or B16/DsRed+ cells.

Example 4

Immunohistochemistry

Tissues were fixed and embedded in OCT or in paraffin blocks as previously described in Lyden et al., "Id1 and Id3 are Required for Neurogenesis, Angiogenesis and Vascularization of Tumor Xenografts," *Nature.* 401:670-677 (1999), which is hereby incorporated by reference in its entirety. For all antigens, the following antibodies were used: VEGFR1 (Flt-1, clone mF-1, ImClone Systems, New York, N.Y. and Flt-1 clone C-17, Santa Cruz Biotechnology), CD31 (PE-CAM, SC-1506, Santa Cruz Biotechnology), VEGFR2 (Flk-1/KDR, dc101, ImClone Systems), MMP-9 (D19557, Oncogene), Id3 (C-20, Santa Cruz Biotechnology), Fibronectin (TV-1, Chemicon), CD11b (CBRM1/5, eBioscience), CD34 (RAM34, BD Pharmigen), ckit (ACK2, eBioscience), PDG-FRα (CD49d, VL-4, PS_2, Southern Biotech), αV (Chemicon), CD133 (13A4, eBioscience), $α_4$ (CD49d, VLA-4, PS_2, Southern Biotech), α5 (CD49e, 5H10-27), α6 (CD49f, GoH3, BD Pharmingen) β1 (9EG7, BD Pharmingen), β2 (M18/2, BD Pharmingen), β4 (Santa Cruz Biotechnology), β7 (M293, BD Pharmingen), SDF-1 (79018.111, R+D systems) CXCR4 (2B11, BD Pharmingen).

Example 5

Double Immunofluorescence

Tissues were sectioned in OCT, and post-fixed with acetone. Washes were with 0.1% BSA/PBS and non-specific antibody blocking with avidin and biotin (Vector Laboratories). The first primary antibody (as detailed above) was incubated overnight at 4° C. Species-specific biotinylated secondary antibodies (Vectastain ABC Kit, Vector) were incubated for 30 min at RT. Texas red Avidin D or Fluorescein Avidin D (Vector) was then incubated for 30 min. This process was repeated for the second primary antibody. Sections mounted with fluorescence mounting media with DAPI (Vectashield, Vector), and visualized as above.

Example 6

Selective Bone Marrow Transplantation

Rosa-26 mice received adeno-VEGF$_{165}$ (AdVEGF) on days 0, 4, and 8 (Avecilla et al., "Chemokine-mediated Interaction of Hematopoietic Progenitors with the Bone Marrow Vascular Niche is Required for Thrombopoiesis," *Nat. Med.* 10:64-71 (2004), which is hereby incorporated by reference in its entirety). On day 12, BM was isolated and labelled with biotinylated murine VEGFR1 antibody and anti-biotin magnetic beads (Miltenyi Biotec) and separated using MACS (Miltenyi Biotec). Purity of VEGFR1+ BM was 95% following three serial passages. The negative selection population represented non-R1 cells (Hattori et al., "Placental Growth Factor Reconstitutes Hematopoiesis by Recruiting VEGFR1 (+) Stem Cells from Bone-marrow Microenvironment," *Nat. Med.* 8:841-9 (2002), which is hereby incorporated by reference in its entirety). WT mice were irradiated and transplanted as described above with the selective BM. Id3 KO (Id1+/+Id3−/−) mice were transplanted with selective Id3 competent VEGFR1+ BM with intravenous injections of $10^5$ cells every three days for a total of 23 days. Control animals were given VEGFR1+ cells without a tumor.

Example 7

Antibody Targeting

WT mice were inoculated with 2×10$^7$ LLC or B-16 cells. For blockade of VEGFR-1, mice were injected intraperitoneally every 48 hours, between day 7 to 22, with rat anti-mouse antibody to VEGFR1 (mf-1, IgG1, 400 µg, ImClone) or VEGFR2 (DC101, IgG1, 800 µg, ImClone) or in combination and then sacrificed on day 24. For blockade of the α4 subunit of VLA-4 mice were injected intravenously day 4, 8, and 12 with rat anti-mouse antibody to CD49d (clone R1-2, IgG$_{2b}$κ, 200 µg, BD Biosciences Pharmingen). Animals were sacrificed on day 14 for evaluation of cluster formation. To target metastasis at a later stage of tumor development, the anti-α4 antibody was injected day 6, 10, 14, 18, and 22, and animals were sacrificed on day 24. All groups were compared to rat anti-mouse IgG$_{2a}$κ isotype control (KLH/G2a1-1, Southern Biotech) administered in the same schedule as the experimental groups.

Example 8

MMP-9 KO

Mice were obtained from Jackson Laboratory with C57BL6 background.

Example 9

In Vitro Aggregation Assays

On day 14, BM-derived VEGFR1+ cells were isolated from mice implanted with B16 cells. R1+ cells (5×10$^5$) were stained fluorescent red (PKH26-GL, Sigma, St. Louis, Mo.) and cultured on 0.2% gelatin in M199 media supplemented with 10% FCS, and incubated with rhVEGF (10 ng/mL, R&D Systems), anti-VEGFR1 (10 µg/ml, mf-1, ImClone), or anti-α4 (CD49, PS_2, 20 µg/ml, Southern Biotec) for 14 hours. Also, studies were performed with incubation of VEGFR1+ cells with rhVEGF, anti-VEGFR1, anti-α4 for 1 hour prior to incubation with tumor cells for 14 hours. The R1+ cells were co-cultured with B-16 or LLC tumor cells, labelled fluorescent green (PKH2-GL, Sigma) (Lee et al., "In Situ Labeling of Adherent Cells with PKH26," *In Vitro Cell. Dev. Biol.—Animal.* 36:4-6 (2000), which is hereby incorporated by reference in its entirety) and analyzed for aggregation and proliferation.

Example 10

Conditioned-Media Studies

Conditioned-media was filtered (0.22µ) from serum-free media cultured on B-16 or LLC cells for 18 hrs, as described in Kessinger et al., "Circulating Factors may be Responsible for Murine Strain-specific Responses to Mobilizing Cytokines," *Exp. Hematology.* 29:775-778 (2001), which is hereby incorporated by reference in its entirety). CM (300 µl) was injected i.p. daily for 9 days into WT mice that had received Rosa-26 BMTs 4 weeks earlier as detailed above. Tissues were stained for fibronectin (TV-1, Chemicon) and β-gal. For tumor redirection studies, i.p. injections of Melanoma CM (300 µl) or PlGF (300 µl, Peprotec) commenced 2 days prior to intradermal implantation of LLC cells and continued daily over the next 21 days. Matched control groups with and without tumor were given serum free media. To inhibit tumor redirection, anti-VEGFR1 antibody was injected, as in the antibody targeting studies, into an experimental group with LLC tumor receiving MCM. Tissues were examined on day 22. As above detailed, above matched control groups with and without tumor were treated with and without antibody.

WT animals were injected with Melanoma conditioned media (300 uL) daily for 7 days prior to tail vein injection of B16 melanoma tumor cells. MCM or serum free RPMI was given to the mice following B16 injection daily until they were sacrificed either at 24 hours or 4 days post-intravenous tumor administration. Lungs were perfused with PBS prior to frozen embedding in OCT.

Example 11

Migration Assays

Migration of VEGFR1 cells in response to conditioned media was next studied. VEGFR1 cells were isolated as above, and 1×10$^5$ cells suspended in serum free media were placed in the upper compartment of 5 µm pore transwells (Costar, Corning Incorporated). Cells were allowed to migrate for 18 hrs with conditioned media or corresponding control media, with cell scraping of the underside of the membrane and lower compartment and trituration with analysis of cell count every 6 hours using hemocytometer and trypan blue. Migration of B16 or LLC tumor cells to VEGFR1+ cells was performed using 12 µm pore transwells as previously described (Redmond et al., "Endothelial Cells Inhibit Flow-induced Smooth Muscle Cell Migration: Role of Plasminogen Activator Inhibitor-1," *Circulation* 103:597-603 (2001), which is hereby incorporated by reference in its entirety). Fluorescently labelled tumor cells (PKH2-GL, Sigma) were seeded at 1×10$^5$ cells into upper chamber, and 1×10$^5$ VEGFR1 cells were plated into lower chamber in serum free media. There was no concentration gradient between the upper and lower chambers. Analysis was performed every 6 hours with direct visualization and manually counting of cells per 200× field using an inverted fluorescent microscope (Nikon Eclipse TE 2000-U).

Example 12

Quantitative PCR Analysis of Fibronectin in Multiple Tissues

Lung tissue was homogenized with a tissue homogenizer in TriZol and RNA was extracted as described previously (Hashimoto et al., "Bone Marrow-derived Progenitor Cells in Pulmonary Fibrosis." *The Journal of Clinical Investigation* 113:243-252 (2004), which is hereby incorporated by reference in its entirety). Fibronectin gene expression was quantified and normalized to GAPDH using TaqMan Gene expression assays (Applied Biosystems) as described previously (Jensen et al., "The Human Herpes Virus 8-encoded Chemokine Receptor is Required for Angioproliferation in a Murine Model of Kaposi's Sarcoma," *Journal of Immunology* 174: 3686-94 (2005), which is hereby incorporated by reference in its entirety).

Example 13

Chemokine Assays

Conditioned media and serum free media as well as tumor-derived plasma were analysed for VEGF and PlGF concentrations by ELISA (Quantikine, R&D Systems) as per manufacturer instructions. Tumor derived plasma was obtained from mice 14 days after LLC or B16 tumor cells.

Example 14

Flow Cytometry Studies

Peripheral blood mononuclear cells were incubated with fluorescently conjugated monoclonal antibodies CD11b (M1/70, PE anti-mouse, BD Pharmingen), Sca-1 (E13-161.7, PE and FITC anti-mouse Ly-6A/E, Becton Dickinson) and VEGFR1 (clone mf-1, FITC, ImClone Systems) as described (Gill et al., "Vascular Trauma Induces Rapid But Transient Mobilization of VEGFR2$^+$ AC133$^+$ Endothelial Precursor Cells," Circulation Research 88:167-174 (2001), which is hereby incorporated by reference in its entirety). Flow cytometry was also performed on the entire right lung after perfusion of the lung with PBS via injection through the right ventricle and were minced into small pieces and filtered with 100 and 40 μm filters (BD Biosciences) to form a single cell suspension as previously described. For cKit flow analysis after a single cell suspension was obtained, cells were stained directly with perCP cKit and then placed in PBS without fixation and analyzed on a Coulter FC500 cytometer.

Example 15

Human Specimens

Human specimens include tumor, adjacent normal (beyond tumor margins), distant normal and lymph nodes. Tissues were embedded in paraffin and fixed frozen as described above and stained with antibodies to VEGFR1 (FB5, ImClone Systems) and Flt-1, Calbiochem. Tissue samples were obtained and handled in accordance with an approved IRB application.

Example 16

Quantitative Immunohistochemistry Analysis

Utilizing both IP Lab and Adobe Photoshop 7.0 random 100× fields were obtained and analyzed by selecting a standardized color range for β-gal or immunohistochemical staining Once this boundary was delineated, the area under the pixilation histogram was calculated, comparing total staining area to total tissue area.

Example 17

Statistical Analysis

Results are expressed as mean±standard error. Data were analyzed by students test and analysis of variance using GraphPad Prism statistical program. P values<0.05 were significant. Error bars depict standard error of the mean.

Figure 1A:
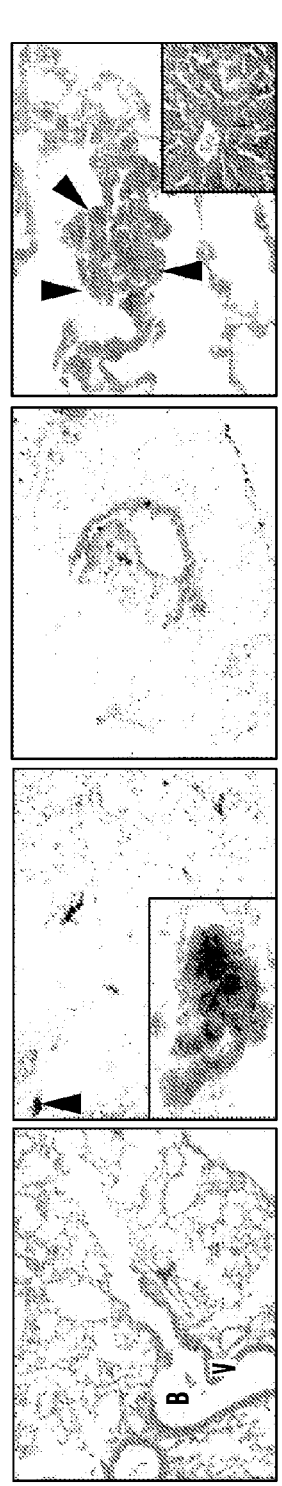
FIGS. 1A-E show bone marrow-derived cells form the pre-metastatic niche.
Figure 1B:
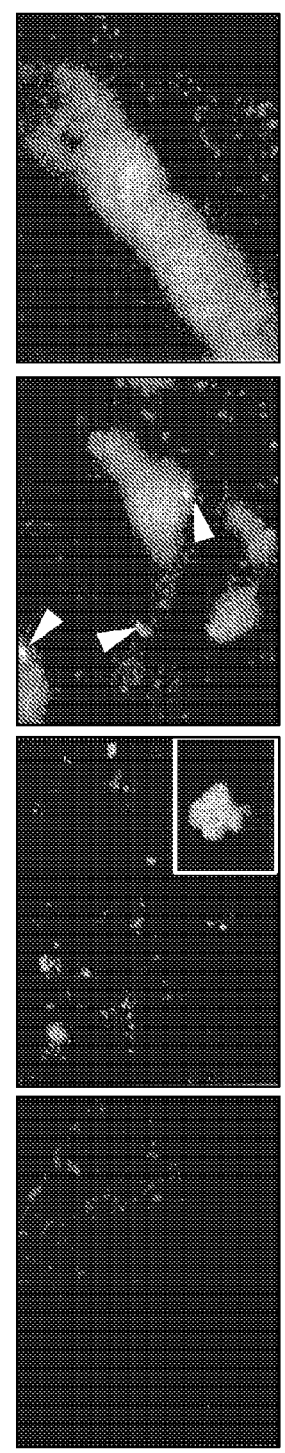

Applicants analyzed the fate of β-galactosidase$^+$ (β-gal$^+$) bone marrow (BM)-derived cells following intradermal primary tumor injection. Either Lewis Lung Carcinoma (LLC) tumor cells, which metastasize specifically to the lung and rarely to the liver, or B16 melanoma tumor cells, that have a more widely disseminated metastatic potential, were used. Lung, liver, spleen, kidney, and gonads were sectioned and stained for the presence of β-gal$^+$ BM cells or screened for GFP$^+$ BM cells following intradermal injection of either tumor type. Following irradiation but prior to tumor implantation, little or no β-gal$^+$ (0.01%±0.01β-gal staining/100× field) or GFP$^+$ BM-derived cells was observed in the lung of mice (FIGS. 1A & 1B left panels). By day 14, post-tumor implantation and prior to the arrival of tumor cells, the extravasation and cluster formation of β-gal$^+$ (3.2%±1.2 β-gal staining/100× field, p<0.05 by Student's t test) or GFP$^+$ BM-derived cells were detected near terminal bronchioles and distal alveoli, both common sites for future metastasis (FIGS. 1A & 1B, left middle panel & inset). By day 16, β-gal$^+$ clusters comprising 20 to 100 cells with organized stromal elements dictate the contours of future metastatic lesions (FIG. 1A, right middle panel). Individual red fluorescent tumor cells, associated with pre-existing BM-derived clusters are visible by day 18 (FIG. 1B, right middle panel) and progress to micrometastases by day 23 (FIGS. 1A & 1B, right panels). The presence of β-gal$^+$ BM cells was maintained even within well-established tumor metastases (FIG. 1A, right panel inset).

Example 18

Bone Marrow-Derived Cells Arrive Prior to Tumor Cell Spread

Figure 1C:
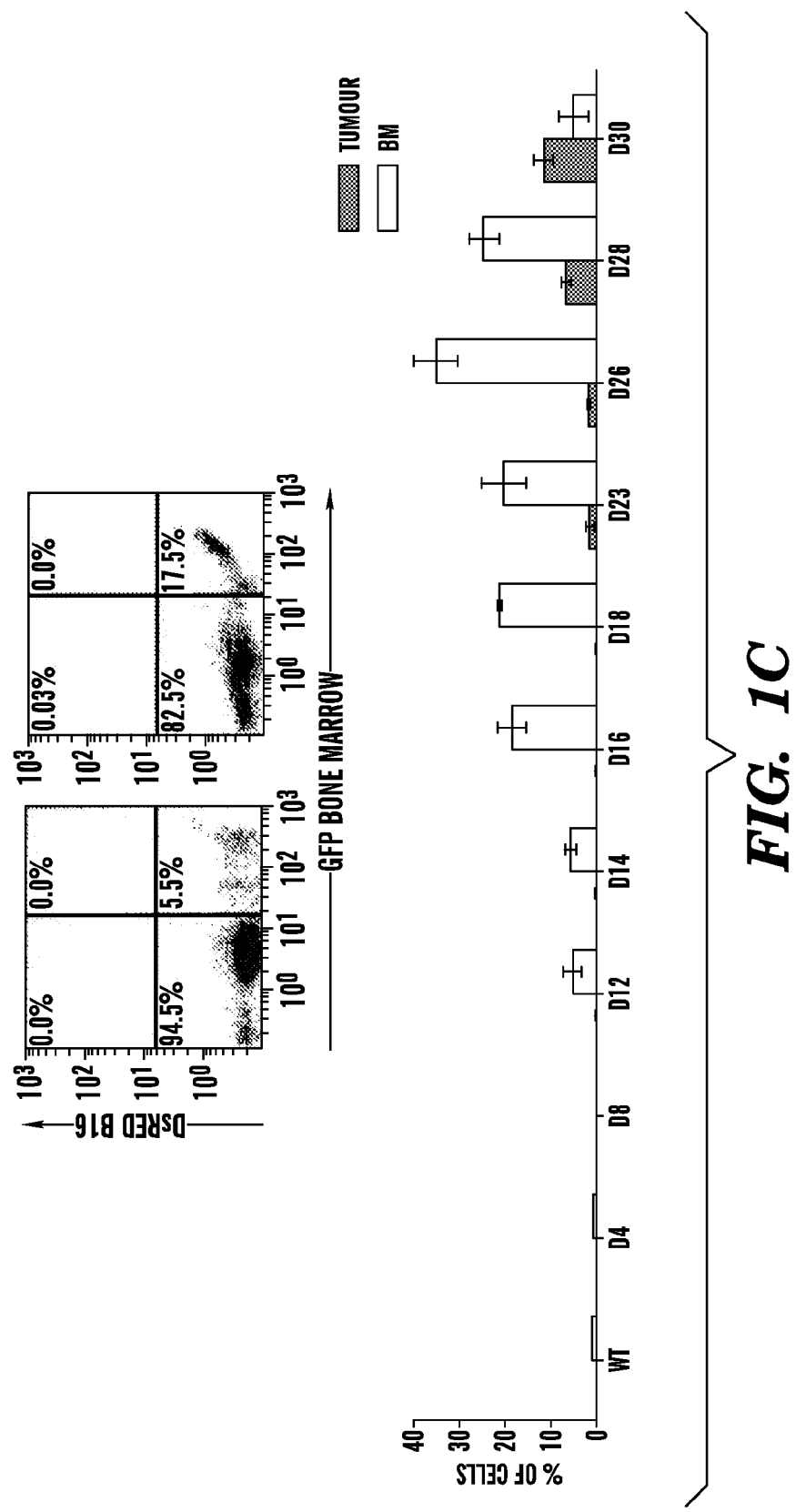
Figure 1D:
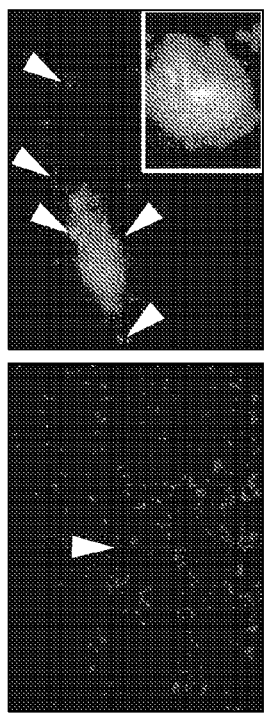

To further define the timing of tumor cell arrival, a flow cytometric study was undertaken to determine the presence of the GFP$^+$ bone marrow-derived cells and the red fluorescently labelled tumor cells. Prior to day 8, minimal GFP$^+$ BM-derived cells are observed in the lung (FIG. 1C left panel & table). Beginning day 12, there is the migration of BM-derived cells into the lung coinciding with the microscopic observation of BM-derived clusters (FIG. 1C). These cells increase in number and are then joined by tumor cells by day 18 (FIG. 1C). No tumor cells were detected either by microscopy or flow cytometry in the lung earlier than day 16. Over time, increasing numbers of tumor cells are identified in the lung via flow cytometry, corresponding to the adherence and proliferation of tumor cells at the site of the established bone marrow-derived clusters as seen in the microphotograph images (FIGS. 1B & 1C). A co-clustering frequency of greater than 95% of tumor cells with GFP$^+$ BM-derived clusters (97%±1.1, FIG. 1B, right panel), was determined. Although it is possible a few tumor cells could be missed using this methodology, further experiments with mice given media conditioned from B16 melanoma cells in culture illustrate that the conditioned media alone can cause mobilization of bone marrow-derived cells and formation of the premetastatic niche. Using a tail vein model of metastasis, introduction of tumor cells after stimulation with conditioned media (FIG. 1D) compared to media alone (FIG. 1D) increases the number of tumor cells at one day post-injection in the lungs (FIG. 1D, 141.3±10.2 tumor cells vs 2.7±0.6 tumor cells/lung cross section, p<0.01 by Student's t test). By four days post-intravenous tumor cell injection, the frequency as well as the size of metastatic nodules in the lung are augmented (207 tumor cells±5.6/lung cross section compared to 14 tumor cells±1.7/lung cross section, p<0.01 by Student's t test). A co-localization analysis for red fluorescent tumor cells to GFP$^+$ clusters was greater than 93% at both time points, indicating that these BM-derived cells assist tumor cell adhesion and proliferation. Therefore, under the influence of factors released by the primary tumor, BM-derived cells enter the bloodstream and mobilize to distant yet specific premetastatic sites.

Example 19

Sites of BM-Derived Cellular Clusters are Tumor Type Specific

Figure 1E:
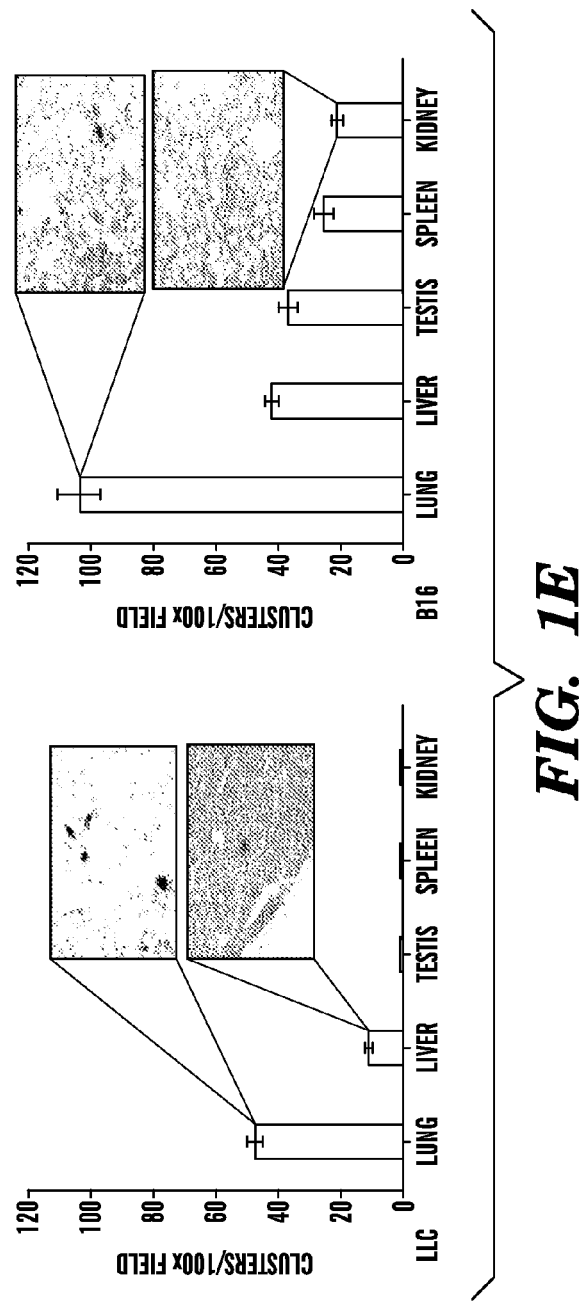

It was examined whether the tumor cell type dictated the distribution of BM clusters to specific premetastatic sites within the body (FIG. 1E). The intradermal injection of LLC tumor cells resulted in the formation of BM clusters limited to only the lung (47.5±2.6/100× field) and liver (10.8±1.1) with no clusters observed in the testis, spleen, or kidney, due to the metastatic specificity of this tumor cell type. In contrast, the B16 melanoma tumor cells induced the formation of BM clusters in multiple organs such as lung (103.8±6.9), liver (41.8±2.4), testis (36.6±3.1), spleen (25±3.2), and kidney (20.6±1.8), corresponding to common organs of metastasis for this tumor (FIG. 1E). Furthermore, B16 melanoma cells, consistent with their more aggressive metastatic nature, induced significantly more clusters than LLC tumor cells ($p<0.01$ by Student's t test).

Example 20

Figure 1G:
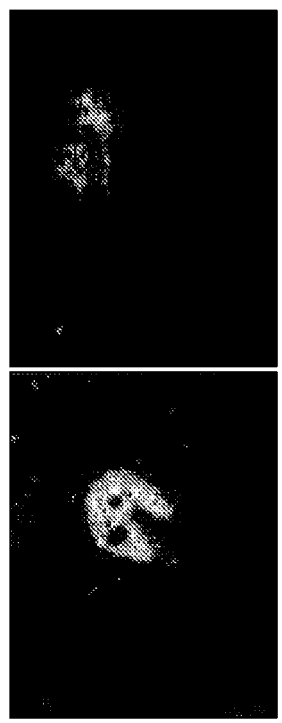
FIGS. 1F-I show that pre-metastatic clusters are comprised of VEGFR1 haematopoietic progenitors.
Figure 1I:
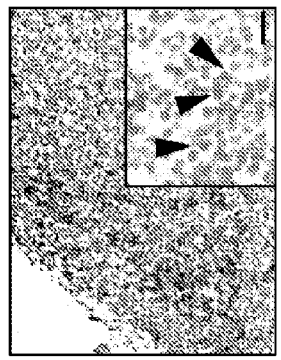
Figure 1I:
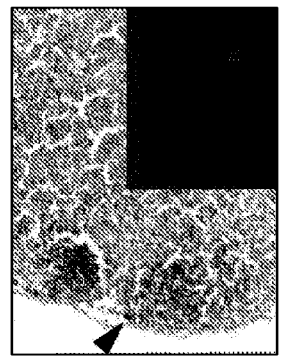
Figure 1I:
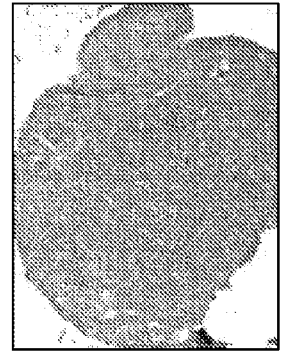
Figure 1F:
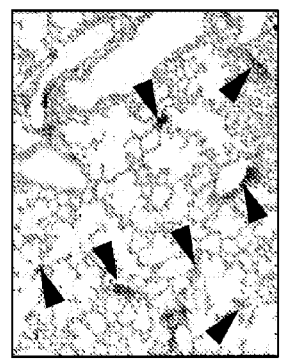
Figure 1H:
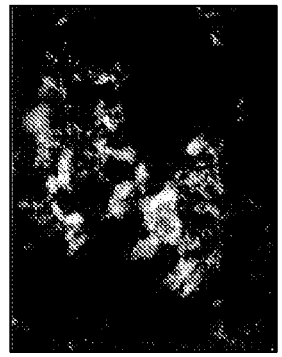
Figure 3F:
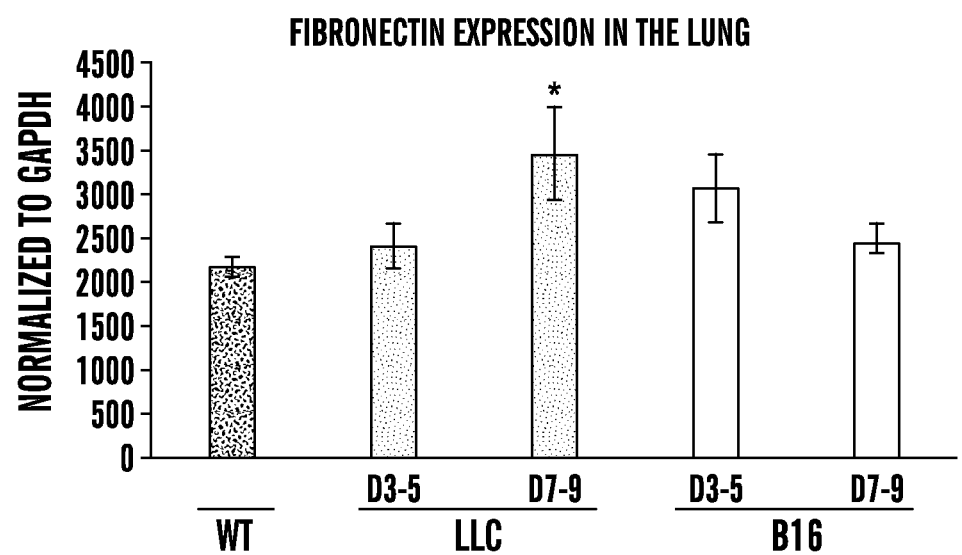

Characterization of these BM-Derived Cells Reveal Hematopoietic Progenitor Status The cellular composition of BM-derived clusters was next characterized. Clusters induced by either tumor cell type expressed VEGFR1 (FIG. 1F, 3.9±0.2 increase above wild type). GFP$^+$ BM-derived clusters co-expressed VEGFR1 (FIG. 1F) compared to little expression of VEGFR1 in the lung parenchyma following irradiation alone (FIG. 1F). Further characterization of these cellular clusters revealed the majority of BM-derived cells that are VEGFR1$^+$ co-express CD133 (FIG. 1G), CD34 (FIG. 1G), and CD117 (cKit) (FIG. 1G & FIG. 1H), suggesting that subsets of these cells are of primitive hematopoietic cell origin. There also appears to be a degree of maturational heterogeneity in the BM-derived clusters, since the myelomonocytic marker CD11b was present on certain cells. Analysis of progenitor cells in the lung after primary tumor implantation recapitulates the time course studies presented previously. As seen by flow cytometry, CD117$^+$ cells arrive in the lung prior to GFP-labelled tumor cells (FIG. 1H). The early VEGFR1$^+$ BM clusters lacked expression of VEGFR2 (FIG. 5A) and CD31 (FIG. 5A). Further kinetic studies revealed that the VEGFR2$^+$ CEPs migrate to the BM-derived clusters coinciding with the arrival of tumor cells (FIG. 5B). The fully formed premetastatic niche contains bone marrow-derived VEGFR2$^+$ endothelial progenitors (FIG. 5). These findings establish that BM-derived VEGFR1$^+$ hematopoietic cells initiate and maintain the premetastatic niche and provide for a permissive microenvironment to initiate and maintain tumor metastasis.

Example 21

BM Derived Clusters Occur in a Spontaneous Tumor Model

The findings of the implanted tumors were compared to those using a spontaneous tumor model. Transgenic mice overexpressing c-Myc were chosen for their early onset and highly aggressive tumor spread throughout the lymph system. By day 40 of life, prominent VEGFR1$^+$ clusters were detected within the lymph nodes prior to the onset of tumor (145.1±16.4 clusters/100× field, FIG. 1I, middle panel and inset) compared to the lack of clusters observed in wild type littermates (0.4±0.3 clusters/100× field, FIG. 1I, left panel, $p<0.001$ by Student's t test). These clusters were not observed in other organs such as lung and liver. By 4 months of life, VEGFR1$^+$ clusters persisted throughout the established lymphomas, but to a lesser extent than in the premetastatic state (67.8±9.5 clusters/100× field in c-Myc mice vs 0.7±0.5 clusters/100× field in littermates, FIG. 1I, right panel and inset, $p<0.001$ by Student's t test). The lymphoma cells surrounding the VEGFR1$^+$ cellular cluster clearly did not express VEGFR1 (FIG. 1I, right panel inset).

Example 22

BM-Derived Cellular Clusters Occur in Common Sites of Metastasis in Human Tissue To validate the data generated in mouse models illustrating the tumor-specific formation of VEGFR1$^+$ cellular clusters, human tissue from patients with primary solid tumors was analyzed. VEGFR1$^+$ clusters were observed both in human primary tumors and metastatic tissue (FIG. 6A; breast carcinoma-axillary lymph node, FIG. 6C; lung carcinoma, FIG. 6E; esophageal carcinoma). There were increased cellular clusters in common sites of metastasis prior to tumor spread, suggesting the malignant potential of this tissue (FIG. 6, Clusters/100× field: FIG. 6B; auxillary lymph node 21±5, FIG. 6D; lung 19±4, FIG. 6F; GE junction 25±4). Normal human lymph nodes and lung tissue obtained from patients without malignancy did not show VEGFR1$^+$ cluster formation (FIGS. 6B, 6D insets).

Example 23

Targeting Selective BM Populations Reveal the Functional Role of VEGFR1$^+$ Cells in Metastasis The potential of purified VEGFR1$^+$ BM cells to initiate premetastatic clusters was assessed by selectively transplanting these progenitors into irradiated mice. By day 24 following LLC implantation, control mice transplanted with intact BM (WT) showed prominent lung metastases (FIG. 2A, left panel) associated with well-established blood vessels (FIG. 2A, left panel inset). Mice transplanted with a purified population of VEGFR1$^+$ BM, however, formed multiple micrometastases throughout the lungs composed of few tumor cells (FIG. 2A, middle panel arrows & table, 25±9 micrometastases/100× field) with aberrant vasculature (FIG. 2A, middle panel inset). This result suggests that VEGFR1$^+$ HPCs are capable of initiating the premetastatic cluster, which can attract tumor cells forming small metastases. In contrast, BM depleted of VEGFR1$^+$ cells failed to produce premetastatic clusters (FIG. 2A right panel & table, $p<0.01$ by one way ANOVA).

To address the issue whether disruption of VEGFR1$^+$ cellular clusters could block metastasis of well-established tumors, LLC or B16 tumor inoculated mice were treated with monoclonal antibodies directed specifically against murine VEGFR1, VEGFR2, or both. This approach allows selective targeting of the VEGFR1$^+$ HPCs, as these tumor cells do not express either VEGFR1 or VEGFR2. By day 24, widespread metastases were evident for both tumor types, as seen in the lungs of animals with LLC (FIG. 2B, left panel & table) or in the spleen of animals with B16 melanoma (FIG. 2B right panel and inset). Anti-VEGFR1 antibody treatment alone eliminated the initiating clusters and prevented metastasis (FIG. 2B & table, $p<0.01$ by one way ANOVA), whereas anti-VEGFR2 antibody did not alter the formation of the VEGFR1+ clusters but prevented the progression of micrometastases (15±11 micromets/clusters/100×) (FIG. 2B, inset & table). The combination of the two antibodies blocked the establishment of the clusters similar to anti-VEGFR1 therapy; however, an isolated B16 metastatic lesion in the lung of one animal was observed (FIG. 2B, inset). Collectively, these results suggest that targeting the VEGFR1+ cell cluster formation can prevent tumor cell adhesion, proliferation, and metastatic spread.

Example 24

VLA4, MMP-9, and Id3 are Involved in the Formation of the Premetastatic Niche

The cellular and molecular mechanisms by which migratory HPCs form cellular clusters as a result of their interaction with the premetastatic microenvironment was next investigated. The interaction of integrin $\alpha_4\beta_1$ (VLA-4) with its ligand fibronectin is essential to the migration of early hematopoietic cells within the bone marrow stroma (Burger et al., "CXCR4 Chemokine Receptors (CD184) and $\alpha_4\beta_1$ Integrins Mediate Spontaneous Migration of Human CD34+ Progenitors and Acute Myeloid Leukaemia Cells Beneath Marrow Stromal Cells (pseudoemperipolesis)," *British Journal of Haematology* 122:579-589 (2003) and Scott et al., "Deletion of $\alpha_4$ Integrins from Adult Hematopoietic Cells Reveals Roles in Homeostasis, Regeneration, and Homing," *Molecular and Cellular Biology* 23:9349-9360 (2003), which are hereby incorporated by reference in their entirety) and mature leukocytes in circulation (Neeson Et Al., "Lymphocyte-Facilitated Tumour Cell Adhesion to Endothelial Cells: The Role of High Affinity Leukocyte Integrins," *Pathology* 35:50-55 (2003) and Jonjic et al., "Molecules Involved in the Adhesion and Cytotoxicity of Activated Monocytes on Endothelial Cells," *The Journal of Immunology* 148:2080-2083 (1992), which are hereby incorporated by reference in their entirety). It was, therefore, assessed whether VEGFR1+ cells might also express integrins, thereby facilitating the interaction of this cell type with the premetastatic niche. It was found that VEGFR1+ HPCs at the premetastatic cluster express VLA-4 (FIG. 3A, and inset, co-expression of VEGFR1) but are negative for $\alpha_v$ integrin. This suggests the expression of VLA-4 on these cells allows for the adhesion of BM-derived cells to the premetastatic niche. Following cluster formation, $\alpha_4\beta_7$ integrin as well as $\alpha_6\beta_4$, also important within bone marrow cells and its associated stroma, are diffusely prominent within the metastatic niche. Proteinases such as matrix metalloproteinase 9 (MMP-9), produced by hematopoietic cells, can serve to breakdown basement membranes and alter local microenvironments by releasing soluble Kit-ligand and VEGF-A to support newly introduced cells expressing cKit (Hessig et al., "Recruitment of Stem and Progenitor Cells from the Bone Marrow Niche Requires MMP-9 Mediated Release of Kit-ligand," *Cell* 109:625-37 (2002) and Bergers et al., "Matrix Metalloproteinase-9 Triggers the Angiogenic Switch During Carcinogenesis," *Nat Cell Biol* 2:737-744 (2000), which are hereby incorporated by reference in their entirety). In addition, metalloproteinase expression can be enhanced through $\alpha_4\beta_1$ signalling due to fibronectin binding (Huhtala et al., "Cooperative Signalling by alpha 5 beta 1 and alpha 4 beta 1 Integrins Regulates Metalloproteinase Gene Expression in Fibroblasts Adhering to Fibronectin," *Journal of Cell Biology* 129:867-879 (1995) and Yakubenko et al., "Differential Induction of Gelatinase B (MMP-9) and Gelatinase A (MMP-2) in T Lymphocytes Upon alpha(4)beta(1)-mediated Adhesion to VCAM-1 and the CS-1 Peptide of Fibronectin," *Exp. Cell Res.* 260:3-84 (2000), which are hereby incorporated by reference in their entirety). Expression of MMP-9 was observed in premetastatic clusters along with VLA-4 distribution suggesting MMP-9 production may be a result of integrin binding and activation in these VEGFR1+ HPCs (FIG. 3A). These findings are in agreement with and expand upon the previous work of Hiratsuka, et. al., that demonstrated a VEGFR1-mediated induction of MMP-9 expression in the premetastatic lung (Hiratsuka et al., "MMP9 Induction by Vascular Endothelial Growth Factor Receptor-1 is Involved in Lung-specific Metastasis," *Cancer Cell.* 2:289-300 (2002), which is hereby incorporated by reference in its entirety).

It has been previously shown that upregulation of Id genes is critical for the mobilization of progenitors for the growth of primary tumors (Ruzinova et al., "Effect of Angiogenesis Inhibition by Id Loss and the Contribution of Bone-marrow-derived Endothelial Cells in Spontaneous Murine Tumours," *Cancer Cell.* 4:277-289 (2003), which is hereby incorporated by reference in its entirety). Consistent with the VLA-4 distribution, expression was also seen for Id3 (FIG. 3A and inset, co-expression of VEGFR1 and Id3) within the clusters. This result suggests that Id3 upregulation may facilitate the mobilization of VEGFR1+ cells to the premetastatic niche. In addition, expression of specific integrins is regulated by Id gene activation and may be responsible for BM-derived cell and stromal cell interactions, motility and recruitment (Ruzinova et al., "Effect of Angiogenesis Inhibition by Id Loss and the Contribution of Bone-marrow-derived Endothelial Cells in Spontaneous Murine Tumours," *Cancer Cell.* 4:277-289 (2003), which is hereby incorporated by reference in its entirety).

To confirm the functional roles of these proteins in establishing the premetastatic niche, expression of VLA-4 (with anti-α4 antibodies) was either inhibited or studied VEGFR1+ cell cluster formation in MMP-9 and Id3 knockout mice. Each of these models was challenged with tumor and found reduced cluster formation (FIG. 3) and metastatic spread three weeks post tumor implantation. Impaired mobilization of HPCs illustrated by the decrease in mobilized VEGFR1+ cells in the circulation of Id mutant mice (654 VEGFR1+ CD11b+ cells/µl) compared to wild type controls (3,283 VEGFR1+CD11b+ cells/µl) in response to tumor inoculation (p<0.01 by Student's t test, FIG. 9) was demonstrated. This confirms the reduction in primary tumor growth seen previously in these animals and serves to explain their reduced metastatic phenotype.

To formally examine the potential of wild-type VEGFR1+ cells to restore the metastatic defect in the Id3−/− mice, Id3 competent GFP+ VEGFR1+ HPCs were injected intravenously in the Id3 KO mice harboring LLC tumors. Introduction of wild-type VEGFR1+ cells alone re-established cluster formation and micrometastases by day 21 post-tumor implantation (FIG. 3B). Notably, the LLC metastatic lesions were associated with the pre-established GFP+ BM-derived clusters (FIG. 3B). These findings further emphasize the functional role of VEGFR1+ BM-derived cells necessary for the establishment of clusters and metastasis.

Example 25

Fibronectin in Tissue Parenchyma Present as a Haptotactic Ligand for VLA-4+ BM-Derived Cells The tissue parenchyma was next examined, following the injection of the primary tumor and prior to the homing of the BM-derived VLA-4+ VEGFR1+ cells, to determine if expression of tissue-specific ligands could mediate adhesion and formation of these BM clusters. Indeed, following LLC injection, increased fibronectin expression was observed over time, from day 3 to day 14, in the vicinity of the future metastatic niche in the lung as compared to baseline fibronectin expression seen in WT lung by both immunohistochemical analysis and by quantitative PCR (FIGS. 3C and 3E). Furthermore, resident fibroblast-like stromal cells (FIG. 3), which proliferate in response to primary tumor (FIG. 3) may contribute to the localized fibronectin. For mice implanted with B16, fibronectin expression in the lung was observed in a similar distribution to mice inoculated with LLC (FIG. 3D). Moreover, it appears that fibronectin is expressed in the VEGFR1$^+$ cluster (FIG. 3D). Increased fibronectin expression was notable in multiple tissues exposed to Melanoma conditioned media such as intestine and oviduct consistent with the more aggressive metastatic nature of B16 tumors to these sites ($p<0.05$ for fibronectin expression on days 3-5 and $p<0.001$ for days 7-9 in oviduct from mice given MCM compared to LCM treated or WT tissue by one way ANOVA and $p<0.001$ for fibronectin expression on days 7-9 in intestinal tissue from mice given MCM compared to LCM treated or WT tissue by one way ANOVA, FIGS. 7A and 7B).

Example 26

VEGFR1+ Cells Promote Tumor Cell Migration, Adherence, and Proliferation

In order to confirm that VEGFR1$^+$ progenitors promote the chemoattraction and attachment of tumor cells, VEGFR1$^+$ cells were isolated and red fluorescently labelled (PKH26-Gl) from mice implanted with tumor (FIG. 8). Within one hour of in vitro co-incubation with green fluorescently labelled (PKH2-GL) B16 or LLC cells, the hematopoietic progenitors aggregated and proliferated (150% increase) and promoted the attachment and proliferation of tumor cells. In contrast, VEGFR1$^+$ HPCs previously cultured in the presence of either anti-VEGFR1 or anti-VLA-4 antibodies blocked this binding affinity and expansion (FIG. 8A). Furthermore, a transwell migration assay was performed whereby fluorescently labelled tumor cells have enhanced mobility in response to bone marrow-derived VEGFR1$^+$ cells (29.6±1.4 tumor cells/200×) compared to non-VEGFR1 cells (11.2±0.4) and media alone (9.9±0.9) (FIG. 8B, $p<0.001$ by one way ANOVA). SDF-1/CXCR4 axis is known to play a prominent role in the homing and retention of BM progenitor cells to certain niches within the bone marrow (Ratajczak et al., "Stem Cell Plasticity Revisted: CXCR4-positive Cells Expressing mRNA for Early Muscle, Liver and Neural Cells 'Hide Out' in the Bone Marrow," *Leukemia.* 18:29-40 (2004), which is hereby incorporated by reference in its entirety). Similar to the movement of hematopoietic stem and progenitor cells from the bone marrow in many physiologic processes utilizing this axis, specific tumor cell types which express CXCR4 may also migrate in this fashion in response to local chemokine gradients (Lapidot et al., "Current Understanding of Stem Cell Mobilization: The Roles of Chemokines, Proteolytic Enzymes, Adhesion Molecules, Cytokines and Stromal Cells," *Experimental Hematology.* 30:973-981 (2002), Balkwill, F., "The Significance of Cancer Cell Expression of the Chemokine Receptor CXCR4," *Seminars in Cancer Biology.* 14:171-179 (2004), and Muller et al., "Involvement of Chemokine Receptors in Breast Cancer Metastasis," *Nature.* 410:50-56 (2001), which are hereby incorporated by reference in their entirety). Within the fully formed premetastatic cluster, containing VEGFR1$^+$ cells, fibroblasts, and fibronectin (as seen in FIG. 1A, left panel), SDF-1 (CXCL12) became highly expressed (FIG. 8C). CXCR4 was identified in a diffuse pattern throughout the established primary melanoma but at a localized region at the "viable" rim for LLC (FIG. 8D). The presence of a chemokine gradient, originating from the premetastatic niche may serve to attract the CXCR4$^+$ tumor cells. These findings suggest that the upregulation of fibronectin, dictated by tumor type, enables the binding of VLA-4$^+$VEGFR1$^+$ hematopoietic clusters necessary for the formation of the premetastatic niche. In addition, interactions between these clusters and tumor cells, via the expression of VEGFR1 and VLA-4 and SDF-1 and CXCR4, support the progression of a premetastatic niche to metastasis.

Example 27

Figure 4A:
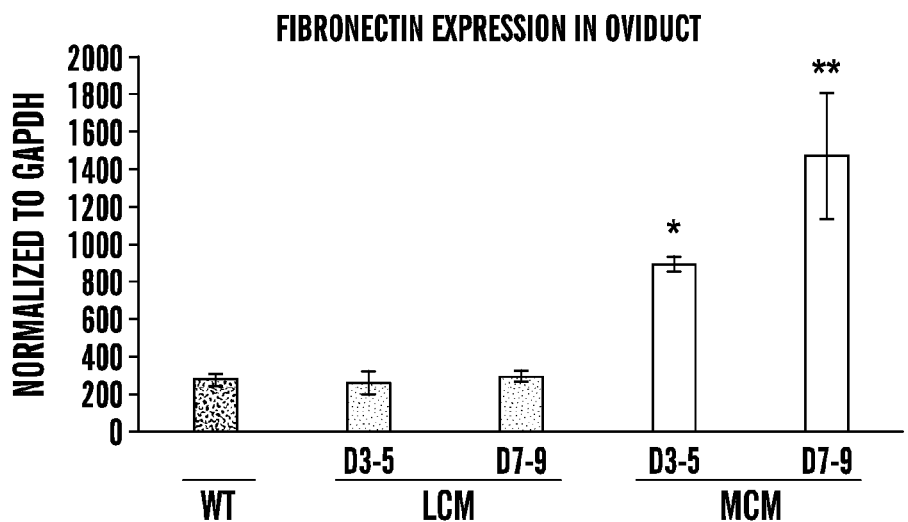
FIGS. 4A-E show redirection of LLC metastases to atypical sites.
Figure 4B:
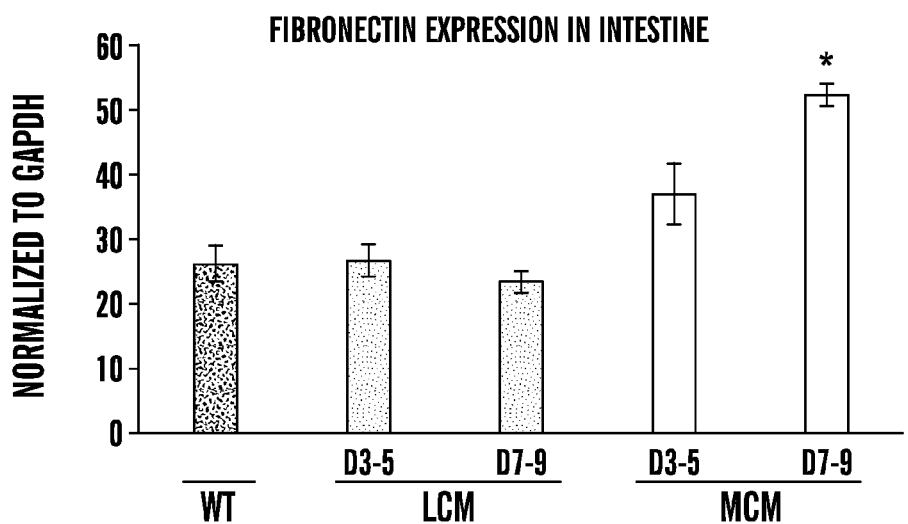
Figure 4C:
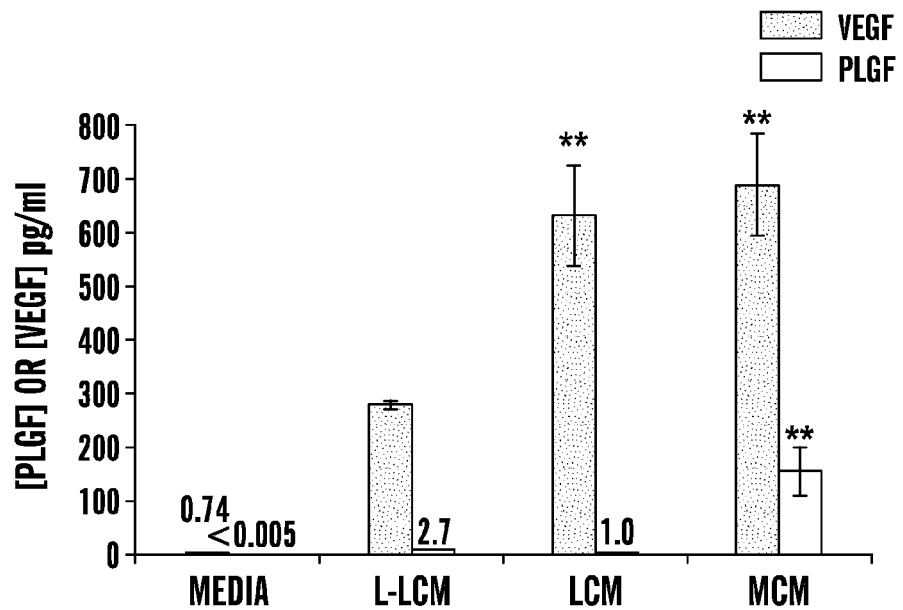
Figure 4D:
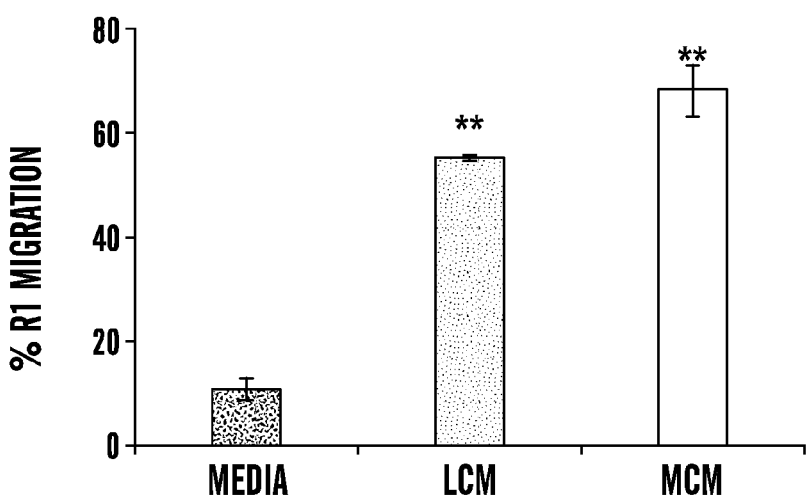
Figure 4E:
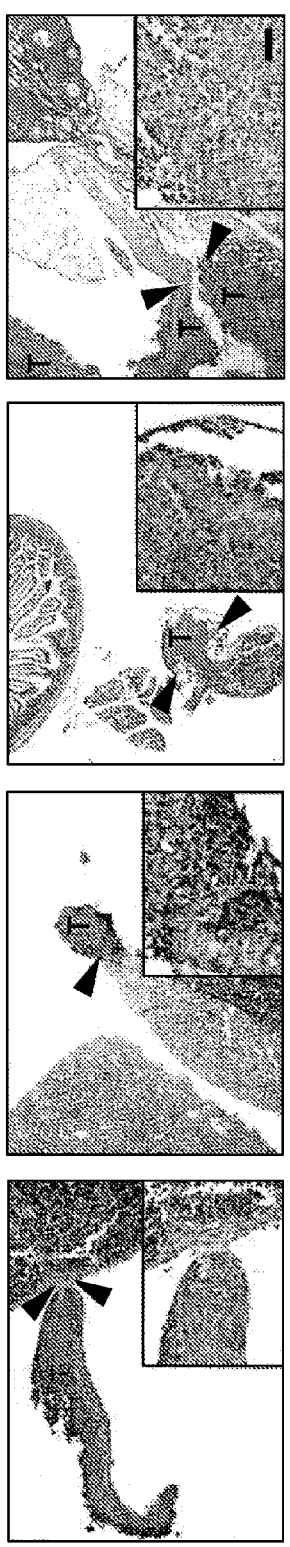

Tumor-Derived Conditioned Media Helps to Dictate Tumor Specific Pattern of Metastatic Spread To further investigate the selective metastatic potential of LLC and B16 cells, conditioned media was obtained from both tumor cell types in culture. The intraperitoneal injection of LLC-conditioned media (LCM) generates the expression of fibronectin, potentially from resident fibroblasts, and BM-derived cluster formation (FIG. 4A), as compared to media alone (FIG. 4), in a similar fashion but more rapidly than primary intradermal LLC. Comparable but accelerated to the effects of intradermal B16 tumors; melanoma conditioned media (MCM) dictates fibronectin expression to a greater extent in the liver than LCM (FIG. 4B). MCM also causes enhanced fibroblast proliferation and fibronectin expression with cluster formation in a wide range of organs, as observed in the intestine (FIG. 4B and FIGS. 7A and 7B) with comparison to media alone (FIG. 4B). This parallels the increased clusters observed in animals with B16 tumors as compared to those with LLC (FIG. 1). Given that MCM promotes cluster formation in a more ubiquitous manner than LCM, it was subsequently investigated whether growth factors varied to help explain the metastatic potential and profile between these two conditioned media (FIG. 4C). High levels of VEGF were found in both condition media groups, higher than plasma from animals with tumors. However, a distinct difference in the level of Placental Growth Factor (PlGF), which signals through VEGFR1 alone, was detected between the two conditioned media. MCM and melanoma-derived plasma contain significantly higher levels of PlGF as compared to little or no PlGF found in LCM and LLC-derived plasma (FIG. 4C). Furthermore, in the low metastatic variant LLC, both VEGF and PlGF were much lower for the condition media and plasma compared to its more aggressive counterpart. In a transwell assay, LCM and MCM enhanced the migration of VEGFR1$^+$ bone marrow-derived cells most effectively when compared to the other growth factor conditions (LCM 55%±0.4, MCM 68.1%±5, media 10.8%±1.7, FIG. 4D, $p<0.001$ by one way ANOVA). Considering these results, it was questioned whether cytokines such as PlGF in MCM were capable of redirecting LLC metastases to non-conventional metastatic sites. MCM given by peritoneal injection prior to LLC intradermal tumor implantation and then daily thereafter resulted in redirecting LLC metastasis from liver and lung to those sites frequently observed in B16 melanoma such as kidney, spleen, intestine, and oviduct (FIG. 4E). In mice with LLC tumor implants and MCM injections, VEGFR1 antibodies blocked cluster formation and prevented the redirected LLC metastases. These results demonstrate that tumor specific chemokines and/or cytokines present in the conditioned media along with the VEGFR1 cellular cluster form another determinant in the complex, multidimensional biochemical and cellular program underlying metastatic spread.

The precise cellular and molecular mechanisms that dictate metastasis of a specific tumor to a pre-determined metastatic location are not known. Many tumors have predilection for metastasis to specific sites. Based on current dogma, metastatic predisposition is believed to reflect inherent molecular differences in tumor cells themselves and the potential influence by the surrounding stromal cells, which include the vasculature, connective tissue and immune cells (Hynes, R. O., "Metastatic Potential: Generic Predisposition of the Primary Tumour or Rare, Metastatic Variants—or Both?," *Cell.* 113:821-3 (2003), Bergers et al., "Benefits of Targeting Both Pericytes and Endothelial Cells in the Tumour Vasculature with Kinase Inhibitors," *J Clin Invest.* 111:1287-95 (2003), Fidler, I., "The Organ Microenvironment and Cancer Metastasis," *Differentiation.* 70:498-505 (2002), Duda et al., "Differential Transplantability of Tumour-associated Stromal Cells." *Cancer Research* 64:5920-5924 (2004), and Folkman, J., "Role of Anigiogenesis in Tumour Growth and Metastasis," *Semin. Oncol.* 29:515-8 (2002), which are hereby incorporated by reference in their entirety). The above results introduce the novel concept that tumor metastasis is initiated by a well-defined sequence of events that is dependent on molecular bookmarking by delivery of VEGFR1+ cells to form specific permissive niches within a target organ. The above data further suggest that differences in tumor secreted humoral factors promote metastatic spread in specific distant organs. Within days following tumor implantation, fibronectin becomes upregulated in certain locations by resident fibroblast and fibroblast-like cells within target organs that are known future sites of metastases, corresponding to the particular primary tumor. Simultaneously, hematopoietic progenitors exit the bone marrow into the peripheral circulation as previously described (Hessig et al., "Recruitment of Stem and Progenitor Cells from the Bone Marrow Niche Requires MMP-9 Mediated Release of Kit-ligand," *Cell.* 109:625-37 (2002), which is hereby incorporated by reference in its entirety). As a result of the niche-specific directional cues from fibronectin, VEGFR1+ HPCs, expressing VLA-4 and producing MMP-9, can traverse established endothelium to form a premetastatic niche prior to the arrival of tumor and VEGFR2+ endothelial cells. These clusters, with MMP-9 production altering the microenvironment, enhanced expression of SDF-1 creating a chemokine gradient, and Id3 activation resulting in integrin upregulation permit the attraction of tumor cells and their incorporation into the niche thereby developing a complete metastatic lesion. As shown, inhibition by a VEGFR1 antibody or the removal of VEGFR1+ cells from the bone marrow prevents the formation of premetastatic clusters and therefore metastases. Moreover, blocking either VEGFR1 or VLA-4 prevents the binding and establishment of the hematopoietic clustered cells and tumor cells. Restoration of the premetastatic niche and metastasis with the introduction of wild-type VEGFR1+ cells into the Id3 knock out mice suggest that the expression of Id3 induces expression of the necessary elements including MMP-9, integrins and possibly chemokines that provide the road map for the homing of the VEGFR1+ cells essential to the establishment of the premetastatic niche.

Recently, much focus has been placed on the role of inflammatory cells in aiding in tumor adherence and invasion into distant organs (Coussens et al., "Inflammation and Cancer," *Nature.* 420:860-867 (2002), Borsig et al., "Synergistic Effects of L- and P-selectin in Facilitating Tumour Metastasis can Involve Non-mucin Ligands and Implicate Leukocytes as Enhancers of Metastasis," *Proc. Natl. Acad. Sci. USA* 99:2193-2198 (2000), Lin et al., "Colony Stimulating Factor 1 Promoted Progression of Mammary Tumours to Malignancy," *J. Exp. Med.* 139:727-740 (2001), and Qian et al., "L-selectin can Facilitate Metastasis to Lymph Nodes in a Transgenic Mouse Model Model of Carcinogenesis," *Proc. Natl. Acad. Sci. USA* 98:3976-3981 (2002), which are hereby incorporated by reference in their entirety). The VEGFR1+ HPCs identified in this study express characteristics common to physiologic pathways of inflammation by providing the necessary adhesion molecules, proteinases, chemokines, and growth conditions, to create a conducive microenvironment for engraftment of tumor cells (Bergers et al., "Matrix Metalloproteinase-9 Triggers the Angiogenic Switch During Carcinogenesis," *Nat Cell Biol.* 2:737-744 (2000), Muller et al., "Involvement of Chemokine Receptors in Breast Cancer Metastasis," *Nature.* 410:50-56 (2001), and Schoppman et al., "Tumour-associated Macrophages Express Lymphatic Endothelial Growth Growth Factors and are Related to Peritumoural Lymphaniogenesis," *Am. J. Pathol.* 161:947-956 (2002), which are hereby incorporated by reference in their entirety). Despite the similarities with inflammation, the premetastatic niche maintains an undifferentiated state as seen with the VEGFR1+ progenitor cell population. This is the first direct evidence that a non-neoplastic cell population can portend a future metastatic site. Furthermore, the identification of hematopoietic clusters in human tissues prior to evidence of tumor spread clearly demonstrates the applicability of targeting VEGFR1 and VLA-4 to identify and prevent metastasis in the clinical setting. This concept will have a tremendous impact on tumor staging and will alter the landscape of adjuvant chemotherapy.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

What is claimed:
1. A method of inhibiting tumor formation in a cancer patient at a site remote from sites of prior tumor formation, said method comprising:
    selecting a cancer patient having an increased blood or tissue level of vascular endothelial growth factor receptor 1+ (VEGFR1+) bone marrow derived progenitor cells compared to a prior measured level of VEGFR1+ bone marrow derived progenitor cells in the patient and
    administering to the selected cancer patient an inhibitor of vascular endothelial growth factor receptor 1+ bone marrow-derived progenitor cells selected from the group consisting of a VEGFR1 inhibitor, a VLA-4 inhibitor, and an MMP-9 inhibitor under conditions effective to inhibit tumor formation in the cancer patient at a site remote from sites of prior tumor formation.
2. The method according to claim 1, wherein said administering is carried out at a time period corresponding to when vascular endothelial growth factor receptor 1+ bone marrow-derived progenitor cell mobilization is stimulated.
3. The method according to claim 2, wherein vascular endothelial growth factor receptor 1+ bone marrow-derived progenitor cell mobilization is stimulated by chemotherapy, stress, surgery, inflammation, irradiation, or growth factors.
4. The method according to claim 3, wherein vascular endothelial growth factor receptor 1+ bone marrow-derived progenitor cell mobilization is stimulated by chemotherapy.

5. The method according to claim 3, wherein vascular endothelial growth factor receptor 1+ bone marrow-derived progenitor cell mobilization is stimulated by stress.

6. The method according to claim 3, wherein vascular endothelial growth factor receptor 1+ bone marrow-derived progenitor cell mobilization is stimulated by surgery.

7. The method according to claim 3, wherein vascular endothelial growth factor receptor 1+ bone marrow-derived progenitor cell mobilization is stimulated by mobilization of inflammatory cells.

8. The method according to claim 3, wherein vascular endothelial growth factor receptor 1+ bone marrow-derived progenitor cell mobilization is stimulated by irradiation.

9. The method according to claim 3, wherein vascular endothelial growth factor receptor 1+ bone marrow-derived progenitor cell mobilization is stimulated by growth factors.

10. The method according to claim 9, wherein the growth factors are selected from the group consisting of granulocyte colony stimulating factors, granulocyte macrophage stimulating factors, and growth hormones that stimulate bone marrow cell growth.

11. The method according to claim 1, wherein the inhibitor of vascular endothelial growth factor receptor 1+ bone marrow-derived progenitor cells binds to vascular endothelial growth factor receptor 1+ bone marrow-derived progenitor cells.

12. The method according to claim 1, wherein the inhibitor of vascular endothelial growth factor receptor 1+ bone marrow-derived progenitor cells prevents or reduces formation of vascular endothelial growth factor receptor 1+ bone marrow-derived progenitor cells.

13. The method according to claim 1, wherein the inhibitor of vascular endothelial growth factor receptor 1+ bone marrow-derived progenitor cells is a vascular endothelial growth factor receptor 1+ bone marrow-derived progenitor cell-specific antibody or antigen-binding portion thereof.

14. The method according to claim 13, wherein a polyclonal antibody is administered.

15. The method according to claim 13, wherein a monoclonal antibody is administered.

16. The method according to claim 13, wherein an antigen-binding portion of an antibody is administered.

17. The method according to claim 1, wherein the inhibitor is an antibody or antigen-binding portion of an antibody capable of binding to VLA-4 ($\alpha 4\beta 1$) integrin.

18. The method according to claim 1, wherein said administering is part of an adjuvant therapy regime.

19. A method of preventing metastases in a cancer patient, said method comprising:
selecting a cancer patient having an increased blood or tissue level of vascular endothelial growth factor receptor 1+ (VEGFR1+) bone marrow derived progenitor cells compared to a prior measured level of VEGFR1+ bone marrow derived progenitor cells in the patient and
administering to the selected cancer patient an inhibitor of vascular endothelial growth factor receptor 1+ bone marrow-derived progenitor cells selected from the group consisting of a VEGFR1 inhibitor, a VLA-4 inhibitor, and an MMP-9 inhibitor under conditions effective to prevent metastases in the cancer patient.

20. The method according to claim 19, wherein said administering is carried out at a time period corresponding to when vascular endothelial growth factor receptor 1+ bone marrow-derived progenitor cell mobilization is stimulated.

21. The method according to claim 20, wherein vascular endothelial growth factor receptor 1+ bone marrow-derived progenitor cell mobilization is stimulated by chemotherapy, stress, surgery, inflammation, irradiation, or growth factors.

22. The method according to claim 21, wherein vascular endothelial growth factor receptor 1+ bone marrow-derived progenitor cell mobilization is stimulated by chemotherapy.

23. The method according to claim 21, wherein vascular endothelial growth factor receptor 1+ bone marrow-derived progenitor cell mobilization is stimulated by stress.

24. The method according to claim 21, wherein vascular endothelial growth factor receptor 1+ bone marrow-derived progenitor cell mobilization is stimulated by surgery.

25. The method according to claim 21, wherein vascular endothelial growth factor receptor 1+ bone marrow-derived progenitor cell mobilization is stimulated by mobilization of inflammatory cells.

26. The method according to claim 21, wherein vascular endothelial growth factor receptor 1+ bone marrow-derived progenitor cell mobilization is stimulated by irradiation.

27. The method according to claim 21, wherein vascular endothelial growth factor receptor 1+ bone marrow-derived progenitor cell mobilization is stimulated by growth factors.

28. The method according to claim 27, wherein the growth factors are selected from the group consisting of granulocyte colony stimulating factors, granulocyte macrophage stimulating factors, and growth hormones that stimulate bone marrow cell growth.

29. The method according to claim 19, wherein the inhibitor of vascular endothelial growth factor receptor 1+ bone marrow-derived progenitor cells binds to vascular endothelial growth factor receptor 1+ bone marrow-derived progenitor cells.

30. The method according to claim 19, wherein the inhibitor of vascular endothelial growth factor receptor 1+ bone marrow-derived progenitor cells prevents or reduces formation of vascular endothelial growth factor receptor 1+ bone marrow-derived progenitor cells.

31. The method according to claim 19, wherein the inhibitor of vascular endothelial growth factor receptor 1+ bone marrow-derived progenitor cells is a vascular endothelial growth factor receptor 1+ bone marrow-derived progenitor cell-specific antibody or antigen-binding portion thereof.

32. The method according to claim 31, wherein a polyclonal antibody is administered.

33. The method according to claim 31, wherein a monoclonal antibody is administered.

34. The method according to claim 31, wherein an antigen-binding portion of an antibody is administered.

35. The method according to claim 19, wherein the inhibitor is an antibody or an antigen-binding portion of an antibody capable of binding to VLA-4 ($\alpha 4\beta 1$) integrin.

36. The method according to claim 19, wherein said administering is part of an adjuvant therapy regime.

37. A method of preventing or inhibiting tumor formation in a cancer patient at a site remote from sites of prior tumor formation, said method comprising:
selecting a cancer patient having had a primary tumor resection and having an increased blood or tissue level of vascular endothelial growth factor receptor 1+ (VEGFR1+) bone marrow derived progenitor cells compared to a prior measured level of VEGFR1+ bone marrow derived progenitor cells in the patient and
administering to the selected cancer patient a VEGFR1 inhibitor, a VLA-4 inhibitor, or an MMP-9 inhibitor under conditions effective to prevent or inhibit tumor formation in the cancer patient at a site remote from sites of prior tumor formation.

38. The method according to claim 37, wherein the inhibitor is an antibody or an antigen-binding portion of an antibody capable of binding to VEGFR1.

39. The method according to claim 1, wherein the inhibitor is an antibody or an antigen-binding portion of an antibody capable of binding to VEGFR1.

40. The method according to claim 19, wherein the inhibitor is an antibody or an antigen-binding portion of an antibody capable of binding to VEGFR1.

* * * * *